United States Patent
Hill et al.

(10) Patent No.: US 8,592,505 B2
(45) Date of Patent: Nov. 26, 2013

(54) HYDROPHOSPHORYLATION OF PHOSPHONOUS ACID DERIVATIVES FOR FLAME RETARDANTS

(75) Inventors: Michael Hill, Cologne (DE); Harald Bauer, Kerpen (DE); Werner Krause, Huerth (DE); Martin Sicken, Cologne (DE)

(73) Assignee: Clariant Finance (BVI) Limited, Tortola (VG)

( * ) Notice: Subject to any disclaimer, the term of this patent is extended or adjusted under 35 U.S.C. 154(b) by 49 days.

(21) Appl. No.: 13/140,563

(22) PCT Filed: Oct. 6, 2009

(86) PCT No.: PCT/EP2009/007145
§ 371 (c)(1),
(2), (4) Date: Jun. 17, 2011

(87) PCT Pub. No.: WO2010/069421
PCT Pub. Date: Jun. 24, 2010

(65) Prior Publication Data
US 2011/0251310 A1    Oct. 13, 2011

(30) Foreign Application Priority Data
Dec. 19, 2008    (DE) .......................... 10 2008 064 012

(51) Int. Cl.
  *C08K 5/00* (2006.01)
  *C08K 5/53* (2006.01)
  *C07F 5/02* (2006.01)
  *C07F 9/28* (2006.01)

(52) U.S. Cl.
  USPC .............. 524/112; 524/133; 562/24; 549/222

(58) Field of Classification Search
  USPC ....................... 524/112, 133; 562/24; 549/222
  See application file for complete search history.

(56) References Cited

U.S. PATENT DOCUMENTS

| | | | |
|---|---|---|---|
| 3,345,432 A | 10/1967 | Gillham et al. | |
| 3,784,638 A | 1/1974 | Lambert | |
| 3,875,263 A | 4/1975 | Herwig et al. | |
| 3,939,050 A | 2/1976 | Kleiner et al. | |
| 3,941,752 A | 3/1976 | Kleiner et al. | |
| 3,962,194 A | 6/1976 | Bollert et al. | |
| 4,001,352 A | 1/1977 | Kleiner et al. | |
| 4,035,343 A | 7/1977 | Bollert et al. | |
| 4,069,245 A | 1/1978 | Dursch et al. | |
| 4,069,247 A | 1/1978 | Kleiner | |
| 4,079,049 A | 3/1978 | Ramsay et al. | |
| 4,168,267 A | 9/1979 | Petrillo | |
| 4,235,991 A | 11/1980 | Digiacomo | |
| 4,337,201 A | 6/1982 | Petrillo | |
| 4,374,131 A | 2/1983 | Petrillo | |
| 4,381,297 A | 4/1983 | Karanewsky et al. | |
| 4,427,665 A | 1/1984 | Karanewsky et al. | |
| 4,555,506 A | 11/1985 | Karanewsky et al. | |
| 4,594,199 A | 6/1986 | Thottathil | |
| 4,602,092 A | 7/1986 | Thottathil et al. | |
| 4,634,689 A | 1/1987 | Witkowski et al. | |
| 5,013,863 A | 5/1991 | Baylis et al. | |
| 5,153,347 A | 10/1992 | Lloyd | |
| 5,190,934 A | 3/1993 | Mickel et al. | |
| 5,229,379 A | 7/1993 | Marescaux et al. | |
| 5,391,743 A | 2/1995 | Ebitino et al. | |
| 5,407,922 A | 4/1995 | Marescaux et al. | |
| 5,545,631 A | 8/1996 | Marescaux | |
| 5,739,123 A | 4/1998 | Norcini et al. | |
| 5,780,534 A | 7/1998 | Kleiner et al. | |
| 6,013,707 A | 1/2000 | Kleiner et al. | |
| 6,090,968 A * | 7/2000 | Horold et al. | ................. 558/137 |
| 6,214,812 B1 | 4/2001 | Karpeisky | |
| 6,355,832 B1 | 3/2002 | Weferling et al. | |
| 6,384,022 B1 | 5/2002 | Jackson et al. | |
| 6,569,974 B1 | 5/2003 | Sicken et al. | |
| 6,727,335 B2 | 4/2004 | Sicken et al. | |
| 6,855,757 B2 | 2/2005 | Horold et al. | |
| 7,446,140 B2 | 11/2008 | Bauer | |
| 7,473,794 B2 | 1/2009 | Wehner et al. | |
| 7,485,745 B2 | 2/2009 | Maas et al. | |
| 7,749,985 B2 | 7/2010 | Gallop et al. | |
| 7,829,736 B2 | 11/2010 | Wehner et al. | |

(Continued)

FOREIGN PATENT DOCUMENTS

AT        243952    12/1965
DE       1494922     6/1969

(Continued)

OTHER PUBLICATIONS

JP-5-230085, Seiji et al. (Jul. 1993), Japan (English Translation).*
PCT International Search Report for PCT/EP2009/007145, mailed Jan. 25, 2010.
English Translation of the PCT International Preliminary Report on Patentability PCT/EP2009/007145 mailed Jun. 30, 2011.
English abstract for JP 05230085, Sep. 7, 1993.
Russian Journal of General Chemistry (translation of Zhurnal Obshchei Khimii), 74(6) pp. 864-872; XP002561442 (2004).
PCT International Search Report for PCT/EP2009/007123, mailed Jan. 29, 2010.

(Continued)

*Primary Examiner* — William Cheung
(74) *Attorney, Agent, or Firm* — Anthony A. Bisulca

(57) ABSTRACT

Addition compounds of a) alkylphosphonous acid derivatives of the formula A-P(=O)(OX)—H (I) and b) diester-forming olefins of formula (II)

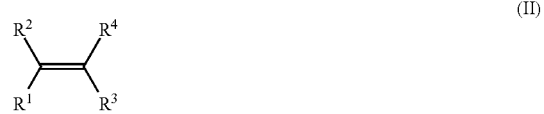

Methods for the production of the addition compounds and the use thereof are also disclosed.

23 Claims, No Drawings

(56) References Cited

U.S. PATENT DOCUMENTS

| | | |
|---|---|---|
| 8,084,518 B2 | 12/2011 | Bauer |
| 8,097,753 B2 | 1/2012 | Maas et al. |
| 2002/0187977 A1 | 12/2002 | Pearlman et al. |
| 2003/0171466 A1 | 9/2003 | Horold et al. |
| 2003/0216533 A1 | 11/2003 | Sicken et al. |
| 2005/0187196 A1 | 8/2005 | Madrid et al. |
| 2006/0084734 A1 | 4/2006 | Bauer et al. |
| 2006/0194973 A1 | 8/2006 | Gainer et al. |
| 2006/0264654 A1 | 11/2006 | Wehner |
| 2007/0210288 A1 | 9/2007 | Maas et al. |
| 2007/0213436 A1 | 9/2007 | Maas et al. |
| 2007/0213563 A1 | 9/2007 | Maas et al. |
| 2008/0183009 A1 | 7/2008 | Wehner et al. |
| 2008/0214708 A1 | 9/2008 | Bauer et al. |
| 2009/0286759 A1 | 11/2009 | Gallop et al. |
| 2010/0093239 A1 | 4/2010 | Bauer et al. |
| 2011/0201732 A1 | 8/2011 | Hill et al. |
| 2011/0201733 A1 | 8/2011 | Hill et al. |
| 2011/0213052 A1 | 9/2011 | Hill et al. |
| 2011/0213059 A1 | 9/2011 | Hill et al. |
| 2011/0213060 A1 | 9/2011 | Hill et al. |
| 2011/0213061 A1 | 9/2011 | Hill et al. |
| 2011/0213062 A1 | 9/2011 | Hill et al. |
| 2011/0213078 A1 | 9/2011 | Hill et al. |
| 2011/0213079 A1 | 9/2011 | Hill et al. |
| 2011/0213080 A1 | 9/2011 | Hill et al. |
| 2011/0224339 A1 | 9/2011 | Hill et al. |
| 2011/0234340 A1 | 9/2011 | Hill et al. |
| 2011/0237720 A1 | 9/2011 | Hill et al. |
| 2011/0237721 A1 | 9/2011 | Hill et al. |
| 2011/0237722 A1 | 9/2011 | Hill et al. |
| 2011/0245385 A1 | 10/2011 | Hill et al. |
| 2011/0245386 A1 | 10/2011 | Hill et al. |
| 2011/0251312 A1 | 10/2011 | Hill et al. |
| 2011/0251314 A1 | 10/2011 | Hill et al. |
| 2011/0251315 A1 | 10/2011 | Hill et al. |
| 2011/0275744 A1 | 11/2011 | Hill et al. |
| 2011/0281983 A1 | 11/2011 | Hill et al. |
| 2012/0064790 A1 | 3/2012 | Bauer et al. |

FOREIGN PATENT DOCUMENTS

| | | |
|---|---|---|
| DE | 2236036 | 2/1974 |
| DE | 2236037 | 2/1974 |
| DE | 2302523 | 2/1974 |
| DE | 2344332 | 3/1975 |
| DE | 2441878 | 3/1976 |
| DE | 2623775 | 12/1976 |
| DE | 2942781 | 4/1980 |
| DE | 10153780 | 11/2002 |
| DE | 19912920 | 9/2009 |
| EP | 00858391 | 8/1983 |
| EP | 0319482 | 6/1989 |
| EP | 0463560 | 1/1992 |
| EP | 0699708 | 3/1996 |
| EP | 0906915 | 4/1999 |
| EP | 0969008 | 1/2000 |
| EP | 1203770 | 5/2002 |
| EP | 1369422 | 12/2003 |
| EP | 1607400 | 12/2005 |
| EP | 1693403 | 8/2006 |
| EP | 1832594 | 9/2007 |
| EP | 1832595 | 9/2007 |
| EP | 1832596 | 9/2007 |
| EP | 1905776 | 4/2008 |
| GB | 1045684 | 10/1966 |
| JP | 05-230085 | * 7/1993 |
| JP | 05230085 | 9/1993 |
| WO | WO 99/28327 | 6/1999 |
| WO | WO 01/42252 | 6/2001 |
| WO | WO 0157050 | 8/2001 |
| WO | WO 02/100871 | 12/2002 |
| WO | WO 2005/014604 | 2/2005 |
| WO | WO 2005/032494 | 4/2005 |
| WO | WO 2005/044830 | 5/2005 |
| WO | WO 2007/052169 | 5/2007 |
| WO | WO 2008/033572 | 3/2008 |
| WO | WO 2008/043499 | 4/2008 |

OTHER PUBLICATIONS

English Translation of the PCT International Preliminary Report on Patentability PCT/EP2009/0071123 mailed May 19, 2011.

Montchamp; "Recent advances in phosphorus-carbon bond formation: synthesis of H-phosphinic acid derivatives from hypophosphus compounds" Journal of Organometallic Chemistry Elsevier-Sequoua S.A. Lausanne, CH, vol. 690; pp. 2388-2406; XP004877374 (May 16, 2005).

Sylvine Deprele et al. "Palladium-Catalyzed Hydrophosphinylation of Alkenes and Alkynes;" Journal of the American Chemical Society, American Chemical Society, Washington DC, US vol. 124, No. 32 p. 9387, XP002500862 (Jan. 1, 2002).

Bravo-Altamirano et al.: "A Novel Approach to Phosphinic Acids from Hypophosphorus Acid;" Tetrahedron Letters, Elsevier, Amsterdam, NL vol. 48, No. 33, pp. 5755-5759, XP022163552 (Jul. 19, 2007).

Sylvine Deprele et al.: "Environmentally Benign Synthesis of H-Phosphinic Acids Using a Water Tolerant, Recyclable Polymer-Supported Catalyst;" Organic Letters, American Chemical Society, US, vol. 6, No. 21, pp. 3805-3808 XP002500861 (Jan. 1, 2004).

Patrice Ribiere et al: "NiCL2-Catalyzed Hydrophosphinylation;" Journal of Organic Chemistry, American Chemical Society, Easton, US, vol. 70, No. 10, pp. 4064-4072, XP002530191 (Jan. 1, 2005).

Courdray L. et al.: "Allylic Phosphinates via Pd-Catalyzed Allylation of H-Phosphinic Acids with Allylic Alcohols; "Organic letters, vol. 10, No. 6, pp. 1123-1126 XP002561368 (Feb. 21, 2008).

Mastalerz: Synthesis of some ethylene-(P,P'-Dialkyl)-Diphosphic Acids as new Potential Antimetabolites of Succinic Acid; Roczniki Chemii Ann. Soc. Chim. Polonorum, vol. 38 pp. 61-66 XP 009126234 (1964).

Kurdyumova et al.: "Synthesis of Phosphinic Acids from Hypophosphites I Acrylates as an Unsaturated Component;" Russian Journal of General Chemistry (Translation of Zhurnal Obshchei Khimii (1997), 67(12) pp. 1852-1856 (Apr. 25, 1997).

Houben-Weyl, vol. 1211, pp. 258-259 (Apr. 22, 1963).

Houben-Weyl, vol. 1211, p. 306 (Apr. 22, 1963).

English abstract of Khairullin et al,"Reaction of chlorides of acids of trivalent phosphorus with conjugated systems I. Reaction of ethylphosphonous dichloride with alpha-beta-unstaturated acids" Zh. Obshch. Khimii. 36, pp. 289-296 (1966).

PCT International search report for PCT/EP2009/007124, mailed Feb. 22, 2010.

PCT International Preliminary Report on Patentability for PCT/EP2009/007124, mailed May 19, 2011.

Piotr Majewski: "A New Method for the Preparation of Bis(1-hydroxyalkyl)-phosphinic Acids;"Synthesis, vol. 6, pp. 555-557, XP002558292 (1987).

Hung Kuei Lin et al.: "Competitive inhibition of interfacial Catalysis by phospholipase A2: differential interaction of inhibitors with the vesicle interface a controlling factor of inhibitor potency" J. Am. Chem. Soc, vol. 115, No. 10, 1993, pp. 3932-3942 XP009126627 (1993).

Kallinowsky G. et al.: "C13 Nuclear Magnetic Resonance Study of Some Phosphinolipids Assignmenta and Conformational Studies;" Magnetic Resonance in Chemistry, vol. 27, No. 7, pp. 647-652 XP002558647 (1989).

PCT International Search Report for PCT/EP2009/007125, mailed Feb. 22, 2010.

English translation of PCT International Preliminary Report on Patentability for PCT/EP2009/007125, mailed May 19, 2011.

PCT International search report for PCT/EP2009/007126, mailed Sep. 2, 2010.

English translation of PCT International Preliminary Report on Patentability for PCT/EP2009/007126, mailed May 19, 2011.

Froestl W. et al.: "Phosphinic Acid Analogues of Gaba. 2. Selective, Orally Acitive Gabab Antagonists," Journal of Medicinal Chemistry, American Chemical Society, Washington, US, vol. 38, No. 17, pp. 3313-3331, XP000999491 (Jan. 1, 1995).

(56) References Cited

OTHER PUBLICATIONS

PCT International Preliminary Report on Patentability for PCT/EP2009/007127, mailed Jan. 18, 2010.
English translation of PCT International Preliminary Report on Patentability for PCT/EP2009/007127, mailed May 19, 2011.
PCT International Preliminary Report on Patentability for PCT/EP2009/007128, mailed Jan. 27, 2010.
English translation of PCT International Preliminary Report on Patentability for PCT/EP2009/007128, mailed May 19, 2011.
PCT International Preliminary Report on Patentability for PCT/EP2009/007129, mailed Feb. 22, 2010.
English translation of PCT International Preliminary Report on Patentability for PCT/EP2009/007129, mailed May 19, 2011.
PCT International Preliminary Report on Patentability for PCT/EP2009/007130, mailed Apr. 29, 2010.
English translation of PCT International Preliminary Report on Patentability for PCT/EP2009/007130, mailed May 19, 2011.
Nifant'ev et al.: "Reactions of acetylenes with hypophosphorous aand phosphous acids;" Journal of General Chemistry USSR Consultants Bureau, New York, NY, US vol. 56 No. 4 pp. 680-688 XP002165520 (Sep. 20, 1986).
English Abstract for DE 2344332, Mar. 27, 1975.
Kabachnik et al.: "Synthesis and properties of some ethylenepiphosphoryl compounds," Russian Chemical Bulletin, vol. 23, No. 10 p. 2205 XP002557075 (1974).
Saratovskikh I. et al.: "Phosphorus-containing Aminocarboxylic Acids: XIV. Synthesis of Analogs of [alpha]-.Substituted Glutamic Acid" Russian Journal of General Chemistry Nauka/Interperiodica, Mo, vol. 75, No. 7 pp. 1077-1084 XP019301159 (Jul. 1, 2005).
Chemical Abstracts Service, Columbus, Ohio, US: Raevskii et al. "Gareev et al. Stereochemistry of a 1,3-dipolar cycloaddition of diazomethane to alpha-substitued vinyluphosphoryl compounds containing a chiral phosphorus atom" XP002567581 (1979).
Chemical Abstracts Service, Columbus, Ohio, US: Raevskii et al. "Electron-donor and acceptor functions of physiologically active and model compounds. V. Calculation of the electron-donor fuction of phosphoryl oxygen" XP002567582 (1984).
Isabelle Abrunhosa Thomas et al.: "Alkylation of H-Phosphinate Esters under Basic Conditions;" Jounal of Organic Chemistry, American Chemical Society, Easton,: US, vol. 72 No. 8 pp. 2851-2856 XP002530192 (Jan. 1, 2007).
Catherine Ruflin et al.: "Tetrakis(trimethylsilyl)hypophosphate P2O2(OTMS)4: Synthesis, reactivity and applicationas flame retardants;" Heteroatom Chemistry, VCH publishers, Defield Beach, FL, US, vol. 18, No. 7 pp. 721-731 XP009118331 (Nov. 6, 2007).
PCT International Search Report for PCT/EP2009/007131, mailed Feb. 8, 2010.
English translation of the PCT International Preliminary Report on Patentablity for PCT/EP2009/007131, mailed May 19, 2011.
PCT International Preliminary Report on Patentability for PCT/EP2009/007132, mailed Feb. 15, 2010.
English translation of PCT International Preliminary Report on Patentability for PCT/EP2009/007132, mailed May 19, 2011.
PCT International Preliminary Report on Patentability for PCT/EP2009/007133, mailed Feb. 3, 2010.
English translation of PCT International Preliminary Report on Patentability for PCT/EP2009/007133, mailed May 19, 2011.
Database Beilstein [Online] Beilstein Institute for Organic Chemistry, Frankfurt-Main, DE; XP002561148, retrived from xfire Database accession No. Reaction ID 198358, abstract (1954).
PCT International Preliminary Report on Patentability for PCT/EP2009/007134, mailed Feb. 18, 2010.
English translation of PCT International Preliminary Report on Patentability for PCT/EP2009/007134, mailed May 19, 2011.
PCT International Preliminary Report on Patentability for PCT/EP2009/007135, mailed Mar. 17, 2010.
English translation of PCT International Preliminary Report on Patentability for PCT/EP2009/007135, mailed May 26, 2011.
Bravo-Altamirano et al.: "Palladium-Catalyzed Reaction of Hypophosphorous Compounds with Allenes, Diene and Allylic Electrophiles: Methodology for the Synthesis of Allylic H-Phosphinates" J. org. Chem., vol. 73, No. 6, pp. 2292-2301 XP002567417 (Feb. 15, 2008).
Nadia Valiaeva et al.: "Phosophinic Acid Pseudopeptides Analogous to Glutamyl-gamma-glutamate: Synthesis and Coupling to Pteroyl Azides Leads to Potent Inhibitors of Folypoly-gamma-glutamate Synthetase;" J. Or. Chem., vol. 66, pp. 5146-5154 XP002567418 (2001).
Yamagishi takehiro et al.: "Stereoselective Synthesis of beta-Amino-alpha-hydroxy(allyl)phosphinates and an Application to the Synthesis of a building Block for Phosphinyl Peptides" Synlett, No. 9, pp. 1471-1474, XP 002567142 (Jan. 1, 2002).
PCT International Search Report PCT/EP2009/007136, mailed Mar. 22, 2010.
English translation of the PCT International Preliminary Report on Patentability for PCT/EP2009/007136, mailed Jun. 16, 2011.
Database Beilstein [online] Beilstein Institute for Organic Chemistry, Frankfurt-Main, DE; Database accession No. Reaction ID 101395 XP 002567148 (1956).
PCT International Search Report for PCT/EP2009/007137, mailed Mar. 12, 2010.
English translation of the PCT International Preliminary Report on Patentability for PCT/EP2009/007137, mailed Jun. 16, 2011.
Yamagishi et al.: "Diastereoselective synthesis of beta-substituted alpha-hydroxyphosphinates through hydrophosphinylation of alpha-heteroatom-substituted aldehydes; " Tetrahedron Elsevier Science Publishers, Amsterdam, NL., vol. 59, No. 6 pp. 767-772 XP004404933 (Feb. 3, 2003).
Database Beilstein [online] Beilstein Institute for Organic Chemistry, Frankfurt-Main, DE; Database accession No. Reaction ID 970178 XP 002571550 (1963).
PCT International Search Report for PCT/EP2009/007139, mailed Mar. 22, 2010.
English translation of the PCT International Preliminary Report on Patentability for PCT/EP2009/007139, mailed Jun. 30, 2011.
PCT International Search Report for PCT/EP2009/007140, mailed Mar. 11, 2010.
English translation of the PCT International Preliminary Report on Patentability for PCT/EP2009/007140, mailed Jun. 30, 2011.
PCT International Search Report for PCT/EP2009/008964, mailed Jul. 9, 2010.
English translation of the PCT International Preliminary Report on Patentability for PCT/EP2009/008964, mailed Jun. 30, 2011.
Alonso et al.: "Transition-Metal Catalyzed Addition of Heteroatom-Hydrogen Bonds to Alkynes;" Chem. Rev., pp. 3148-3153 XP002556525 (2004).
Pudovick et al.: "Free Radical Reaction of Addition of Partial Esters of Phosphorus Acids to Acetylenic Hydrocarbons;" J. Gen. Chem. Ussr, vol. 39, No. 5, pp. 986-988 XP009126232 (1969).
Database Beilstein [online] Beilstein Institute for Organic Chemistry, Frankfurt-Main, DE; Database accession No. Reaction BRN 3110535, retrieved from xfire XP002557076 (1967).
Database Beilstein [Online] Beilstein Institute for Organic Chemistry, Frankfurt-Main, DE; Database accession No. Reaction BRN 8075738 XP 002557077 (1997).
PCT International Search Report for PCT/EP2009/007142, mailed Feb. 9, 2010.
English translation of PCT International Preliminary Report on Patentability for PCT/EP2009/007142, mailed Jun. 30, 2011.
English Abstract for SU 314758, Sep. 21, 1971.
Sasse K Ed —Sasse K: "Houben-Weyl Methoden der Organischen Chemie", Organische Phosphor-Verbindungen; [Methoden der Organischen Chemie], Stuttgart, G. Thieme Verlag DE, XP002500739, pp.257-259, 261, 294-301 (Jan. 1, 1963).
"1" In: Sasse K Ed —Sasse K: "Houben-Weyl Methoden der Organischen Chemie;" Organische Phosphor-Verbindungen; [Methoden der Organischen Chemie], Stuttgart, G. Thieme Verlag, DE, p. 358, XP002564325 (Jan. 1, 1963).
Regitz:"Houben-Weyl Methoden der Organischen Chemie" Organische Phosphor-Verbindungen; [Methoden der Organischen Chemie], Stuggart, G. Thieme Verlag, DE, pp. 308-309 XP002564334 (Jan. 1, 1982).

(56) References Cited

OTHER PUBLICATIONS

Yamagishi et al.: "Lipase-catalyzed kinetic resolution of alpha-hydroxy-H-phosphinates" Tetrahedron Letters, Elsevier, Amsterdam, NL, vol. 45, No. 36, pp. 6713-6716 XP004556626 (Aug. 30, 2004).

Anderson et al.: "Antidiabetic agents: a new class of reversible carnitine palmitoyltrasferase I inhibitors;" J. Med. Chem., vol. 38, No. 18, pp. 3448-3450 XP002564326 (1995).

Karanewsky et al.: "Synthesis of Phosphinic Monoesters from Phosphonous Acids" Tetrahedron Letters, Elsevier, Amsterdam, NL, vol. 27, No. 16, pp. 1751-1754 XP001084930 (Jan. 1, 1986).

Issleib, et al.: "Synthese und Reaktionsverhalten der Athylen-bis-organophosphine;" Chemische Berichte, vol. 101, pp. 2197-2202 XP009126251.

PCT International Search Report for PCT/EP2009/007143, mailed Feb. 17, 2010.

English translation of the PCT International Preliminary Report on Patentability for PCT/EP2009/007143, mailed Jun. 30, 2011.

Regitz: "Houben-Weyl Methoden der Organishcen Chemie" p. 188, (Jan. 1, 1982).

Rezanka et al.: "Synthesis of a Bifunctional Monophosphinate DOTA Derivative Having a Free Carboxylate Group in the Phosphorus Side Chain;" Synthesis, Georg Thieme Verlag, Stuttgart pp. 1431-1435 XP009126087 (Sep. 1, 2008).

Database Beilstein [online]Beilstein Institute for Organic Chemistry, Frankfurt-Main, DE; Database accession No. Reaction ID 938840 XP002557780 (1962).

Diel et al.: "Organische Phosphorverbindungen 84. Herstellung Eigenschaften und Biologische Wirkung von Hydrazino-Methyl-Phosphon- und Phosphinsaeuren und Derivatin;" Phosphorus and Sulfur and the Related Elements, Gordon and Breach—Harwood Academic, CH, vol. 36, pp. 85-98 XP001105809 (Jan. 1, 1998).

Sasse K Ed —Sasse K: "Houben-Weyl Methoden der Organischen Chemie", Organische Phosphor-Verbindungen; [Methoden der Organischen Chemie], Stuttgart, G. Thieme Verlag De, XP002557781, pp. 228-229 (Jan. 1, 1963).

Kielbasinski et al: "Enzymatic reactions in ionic liquids: lipase-catalysed kinetic resolution of racemic, P-chiral hydroxymethanephosphinates and hydroxmethylphosphine oxides;" Tetrahedron Asymmetry, Pergamon Press Ltd, Oxford, GB, vol. 13, No. 7, pp. 735-738 XP004354866 (May 2, 2002).

Maier: "Organic Phosphorus compounds 91.1 Synthesis and Properties of 1-Amino-2-Arylethylphosphinic and—Phosphinic Acids as well as Phosphine Oxides;" Phosphorus, Sulfur and Silicon and the Related Elements, Gordon and Breach Science Publishers, Amsterdam, GB, vol. 53, No. 1/04 pp. 43-67 XP000671624 (Jan. 1, 1990).

US 6,248,921, 06/2001, Weferling et al. (withdrawn)

* cited by examiner

HYDROPHOSPHORYLATION OF PHOSPHONOUS ACID DERIVATIVES FOR FLAME RETARDANTS

This Application is the National Stage filing under 35 U.S.C. Section 371 of International Application No. PCT/EP2009/007145, filed on Oct. 6, 2009, which claims the benefit of earlier filing date and right of priority to Germany Application No. 10-2008-064 012.3, filed on Dec. 19, 2008.

This invention relates to halogen-free adducts of alkylphosphonous acid derivatives and diester-forming olefins, to halogen-free processes for their preparation and to their use.

Only some adducts of alkylphosphonous acid derivatives and diester-forming olefins are known, since these adducts were hitherto obtainable only with great difficulty, if at all. More particularly, they could hitherto not be prepared free of halogen.

Adducts of oxa-10-phosphaphenanthrene with diester-forming olefins are known, as are processes for their preparation. The technical disadvantage of these adducts is their low phosphorus content which is very important for flame retardancy for example. This makes the use of higher concentrations of adducts necessary and can adversely affect the primary properties of the articles, more particularly polymers, to be protected from the action of flames.

Adducts of methylphosphonous acid and esters onto acrylic acid derivatives are known. However, the acrylic acid derivatives are not dicarboxylic ester formers, but are monocarboxylic ester formers. Dicarboxylic ester formers can be incorporated into polymer chains via two carboxylic acid groups, monocarboxylic ester formers only via the phosphinic acid group and one carboxylic acid group. Dicarboxylic acid-linked products are linked more hydrolysis-resistant in the polymer than products linked with just one carboxylic acid.

The abovementioned methylphosphonous acid is prepared in a halogen-using process whereby the alkyl radical is attached to the phosphorus atom by chemical reaction of yellow phosphorus with haloalkanes. Halogen-using processes of this kind have serious disadvantages in that, more particularly, the halogen compound releases toxic and corrosive gases in the event of a fire. Halogen impurities are in principle disadvantageous for the use of the products, more particularly for use of the products as synthons in flame retardancy applications.

When used as a synthon, the corrosive effect of halide (particularly chloride) ions requires the use of technically very inconvenient and costly materials of construction in order that safety may be ensured.

In relation to flame retardancy applications, halide impurities are responsible for several disadvantages:

In the course of processing (compounding, injection molding of flame-retardant thermoplastic polymeric molding compositions) into flame-retardant polymeric moldings, films, threads and fibers, increased corrosion can lead to destruction of production apparatus.

Corrosion prevents or greatly curtails possible uses in the electronics sector.

When used in the event of fire, hydrohalic-containing combustion gases harmful to health and the environment can be formed.

Adducts of alkylphosphonous acid derivatives and diester-forming olefins can thus only achieve wide use if they can be prepared free of halogen.

It is an object of the present invention to provide halogen-free adducts of alkylphosphonous acid derivatives and diester-forming olefins and more particularly halogen-free processes for their preparation whereby the desired adducts are obtainable in a particularly simple and economical manner and also in appropriately high yields. The target products are halogen-free, unlike those obtainable according to the prior art.

Particularly adducts of alkylphosphonous acid derivatives and diester-forming olefins having short side chains shall be obtainable according to the present invention reproducibly and with good yields.

It has now been found that, surprisingly, the adducts of the present invention are readily obtainable by the process of the present invention.

The technical advantage of the adducts of the present invention over adducts of oxa-10-phosphaphenanthrene, for example, resides in their higher phosphorus content. The phosphorus content of the present invention itaconic acid adduct of ethylphosphonous acid relates to that of oxa-10-phosphaphenanthrene like 155 to 100.

Since the process of the present invention is a halogen-free process, all the disadvantages described above for products comprising halogen-containing radicals/residues are foreclosed in the products of the present invention.

The present invention therefore relates to adducts of alkylphosphonous acid derivatives and diester-forming olefins, their acids, esters and salts or mixtures thereof.

The present invention accordingly provides adducts formed from
a) alkylphosphonous acid derivatives of formula (I)

$$A\text{-}P(=O)(OX)\text{---}H \tag{I}$$

where
A represents $C_2$-$C_{18}$-alkyl, $C_2$-$C_{18}$-alkylene, $C_6$-$C_{18}$-arylalkyl, $C_6$-$C_{18}$-arylalkyl, optionally substituted, and
X represents H, $C_1$-$C_{18}$-alkyl, $C_6$-$C_{18}$-aryl, $C_6$-$C_{18}$-arylalkyl, $C_6$-$C_{18}$-alkylaryl, $C_2$-$C_{18}$-alkylene optionally substituted, Mg, Ca, Al, Sb, Sn, Ge, Ti, Fe, Zr, Zn, Ce, Bi, Sr, Mn, Cu, Ni, Li, Na, K, H and/or a protonated nitrogen base, and
b) diester-forming olefins of formula (II)

where $R^2$, $R^4$ are the same or different and represent $CO_2H$, $CO_2R^5$, $R^6$—$CO_2H$, $R^6$—$CO_2R^5$ and
$R^1$, $R^3$ are the same or different and represent H, $R^5$; or
$R^1$, $R^4$ are the same or different and represent $CO_2H$, $CO_2R^5$, $R^6$—$CO_2H$, $R^6$—$CO_2R^5$ and
$R^2$, $R^3$ are the same or different and represent H, $R^5$; or
$R^2$, $R^4$ are the same or different and represent —CO—O—CO—, —CO—S—CO—, —CO—NR$^1$—CO—, —CO—PR$^1$—CO— and $R^1$, $R^3$ are the same or different and represent H, $R^5$; or
$R^1$, $R^2$ are the same or different and represent $CO_2H$, CN, $CO_2R^5$, $R^6$—$CO_2H$, $R^6$—$CO_2R^5$ and
$R^3$, $R^4$ are the same or different and represent H, $R^5$; or
$R^1$, $R^2$ are the same or different and represent —CR$_2^3$—CO—O—CO—, —CR$_2^3$—CO—NR$^1$—CO—, —CR$_2^3$—CO—O—CO—CR$_2^3$, —CR$_2^3$—CO—NR$^1$—CO—CR$_2^3$ and $R^3$, $R^4$ are the same or different and represent H, $R^5$; or
$R^2$ and $R^4$ each represent —CO—CR$^5$=CR$^5$—CO— and $R^1$, $R^3$ are the same or different and represent H, $R^5$;

$R^5$ represents $C_1$-$C_{18}$-alkyl, $C_6$-$C_{18}$-aryl, $C_6$-$C_{18}$-arylalkyl, $C_6$-$C_{18}$-alkylaryl;

$R^6$ represents $C_2$-$C_{18}$-alkylene, $C_6$-$C_{18}$-arylene, $C_6$-$C_{18}$-alkarylene and/or $C_6$-$C_{18}$-aralkylene.

Preferably A comprises an ethyl, n-propyl, i-propyl, n-butyl, i-butyl, n-pentyl, i-pentyl, n-hexyl, i-hexyl, 2-phenylethyl, 1-phenylethyl, 3-phenylpropyl, 2-phenylpropyl, 2-hydroxyethyl, 3-hydroxypropyl, 2-carboxyethyl, 3-carboxypropyl, 2-acetatoethyl, 3-acetatopropyl, 2-butyratoethyl, 3-butyratopropyl, 2-ethyloxyethyl, 3-ethyloxypropyl, 2-propyloxyethyl, 3-propyloxypropyl, 2-butyloxyethyl, 3-butyloxypropyl, 3-carboxypropyl, 2-aminoethyl and/or 3-aminopropyl group.

Preferably X comprises hydrogen, a methyl, ethyl, propyl, butyl, amyl, octyl, ethylhexyl, ethylene glycol, propylene glycol, butylene glycol, benzyl, phenyl, vinyl or allyl group, lithium, sodium, potassium, magnesium, calcium, barium, aluminum, lead, titanium, iron, zinc, ammonium, anilinium, trimethylammonium, triethylammonium, tripropylammonium, tributylammonium, tetramethylammonium, tetraethylammonium, tetrapropylammonium, tetrabutylammonium, trimethylsilylammonium or N-ethylpiperidine.

Preferably, the diester-forming olefins comprise maleic acid, fumaric acid, itaconic acid, phenylmethylenemalonic acid, their dimethyl, diethyl, dipropyl, diisopropyl and dibutyl esters, maleic anhydride, itaconic anhydride, benzoquinone, naphthoquinone or anthraquinone.

The present invention also provides a halogen-free process for preparing adducts of alkylphosphonous acid derivatives (I) and diester-forming olefins (II) according to one or more of claims 1 to 4, which process comprises a) reacting a phosphinic acid source with non-diester-forming olefins (III) in the presence of a catalyst A to form an alkylphosphonous acid derivative (I), b) reacting the resulting alkylphosphonous acid derivative (I) with diester-forming olefins (II) in the presence of a catalyst B to form the adduct, wherein the alkylphosphonous acid derivatives conform to formula (I)

$$A\text{-}P(=O)(OX)\text{---}H \tag{I}$$

where

A represents $C_2$-$C_{18}$-alkyl, $C_2$-$C_{18}$-alkylene, $C_6$-$C_{18}$-arylalkyl, $C_6$-$C_{18}$-arylalkyl optionally substituted, and X represents H, $C_1$-$C_{18}$-alkyl, $C_6$-$C_{18}$-aryl, $C_6$-$C_{18}$-arylalkyl, $C_6$-$C_{18}$-alkylaryl, $C_2$-$C_{18}$-alkylene optionally substituted, and the catalyst A comprises transition metals, transition metal compounds and/or catalyst systems composed of a transition metal and/or a transition metal compound and at least one ligand, and the catalyst B comprises peroxide-forming compounds, peroxo compounds, azo compounds, alkali metals, alkaline earth metals, alkali metal hydrides, alkaline earth metal hydrides and/or alkoxides.

Preferably, A comprises an ethyl, n-propyl, i-propyl, n-butyl, i-butyl, n-pentyl, i-pentyl, n-hexyl, i-hexyl, 2-phenylethyl, 1-phenylethyl, 3-phenylpropyl, 2-phenylpropyl, 2-hydroxyethyl, 3-hydroxypropyl, 2-carboxyethyl, 3-carboxypropyl, 2-acetatoethyl, 3-acetatopropyl, 2-butyratoethyl, 3-butyratopropyl, 2-ethyloxyethyl, 3-ethyloxypropyl, 2-propyloxyethyl, 3-propyloxypropyl, 2-butyloxyethyl, 3-butyloxypropyl, 3-carboxypropyl, 2-aminoethyl and/or 3-aminopropyl group.

Preferably, X comprises hydrogen, a methyl, ethyl, propyl, butyl, amyl, octyl, ethylhexyl, ethylene glycol, propylene glycol, butylene glycol, benzyl, phenyl, vinyl and/or allyl group, lithium, sodium, potassium, magnesium, calcium, barium, aluminum, lead, titanium, iron, zinc, ammonium, anilinium, trimethylammonium, triethylammonium, tripropylammonium, tributylammonium, tetramethylammonium, tetraethylammonium, tetrapropylammonium, tetrabutylammonium, trimethylsilylammonium or N-ethylpiperidine.

Preferably, the diester-forming olefins conform to formula (II)

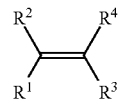

(II)

where $R^2$, $R^4$ are the same or different and represent $CO_2H$, $CO_2R^5$, $R^6$—$CO_2H$, $R^6$—$CO_2R^5$ and $R^1$, $R^3$ are the same or different and represent H, $R^5$; or $R^1$, $R^4$ are the same or different and represent $CO_2H$, $CO_2R^5$, $R^6$—$CO_2H$, $R^6$—$CO_2R^5$ and $R^2$, $R^3$ are the same or different and represent H, $R^5$; or $R^2$, $R^4$ are the same or different and represent —CO—O—CO—, —CO—S—CO—, —CO—NR$^1$—CO—, —CO—PR$^1$—CO— and $R^1$, $R^3$ are the same or different and represent H, $R^5$; or $R^1$, $R^2$ are the same or different and represent $CO_2H$, CN, $CO_2R^5$, $R^6$—$CO_2H$, $R^6$—$CO_2R^5$ and $R^3$, $R^4$ are the same or different and represent H, $R^5$; or $R^1$, $R^2$ are the same or different and represent —$CR_2^3$—CO—O—CO—, —$CR_2^3$—CO—NR$^1$—CO—, —$CR_2^3$—CO—O—CO—$CR_2^3$, —$CR_2^3$—CO—NR$^1$—CO—$CR_2^3$ and $R^3$, $R^4$ are the same or different and represent H, $R^5$; or $R^2$ and $R^4$ each represent —CO—$CR^5$=$CR^5$—CO— and $R^1$, $R^3$ are the same or different and represent H, $R^5$;

$R^5$ represents $C_1$-$C_{18}$-alkyl, $C_6$-$C_{18}$-aryl, $C_6$-$C_{18}$-arylalkyl, $C_6$-$C_{18}$-alkylaryl;

$R^6$ represents $C_2$-$C_{18}$-alkylene, $C_6$-$C_{18}$-arylene, $C_6$-$C_{18}$-alkarylene and/or $C_6$-$C_{18}$-aralkylene.

Preferably, the diester-forming olefins comprise maleic acid, fumaric acid, itaconic acid, phenylmethylenemalonic acid, their dimethyl, diethyl, dipropyl, diisopropyl and dibutyl esters, benzoquinone, naphthoquinone or anthraquinone.

Preferably, the phosphinic acid source comprises phosphinic acid, a salt of phosphinic acid, an ester of phosphinic acid or mixtures thereof.

Preferably, the non-diester-forming olefins conform to formula (III)

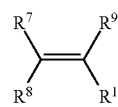

(III)

where $R^7$ to $R^{10}$ are the same or different and represent $C_1$-$C_{18}$-alkyl, $C_6$-$C_{18}$-aryl or $C_2$-$C_{18}$-alkylene.

Preferably, the non-diester-forming olefins (III) comprise ethylene, 1-propylene, 1-butene, 1-pentene, 1-hexene and/or 1,3-butadiene.

Preferably, the transition metals and/or transition metal compounds comprise those from the seventh and eighth transition groups.

Preferably, the transition metals and/or transition metal compounds comprise rhodium, nickel, palladium, ruthenium and/or platinum.

Preferably, the catalyst B comprises hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-t-butyl peroxide and/or peroxodisulfuric acid, and/or comprises azobisisobutyronitrile, 2,2'-azobis(2-amidinopropane)dihydrochloride and/or 2,2'-azobis(N,N'-dimethyleneisobutyramidine)dihydrochloride and/or comprises lithium, lithium hydride, lithium aluminohydride, methyllithium, butyllithium, t-butyllithium, lithium diisopropylamide, sodium, sodium hydride, sodium borohydride, sodium methoxide, sodium ethoxide, sodium butoxide, potassium methoxide, potassium ethoxide and/or potassium butoxide.

Preferably, the reaction product obtained from alkylphosphonous acid derivatives (I) and diester-forming olefins (II) after step b) is reacted with an ester former in a step c).

Preferably, the ester formers comprise $C_1$-$C_{20}$ saturated and unsaturated mono-, di-, tri- and tetrahydric alcohols.

Preferably, the ester formers comprise methanol, ethanol, propanol, butanol, amyl alcohol, octanol, ethylene glycol, polyethylene glycol, 1,2-propanediol, 1,3-propanediol, butanediol, glycerol, erythritol, pentaerythritol, allyl alcohol, 3-buten-1-ol, 3-hydroxy-1-butene, 3-buten-2-ol, methylvinylcarbinol, 2-methyl-2-propen-1-ol, methallyl alcohol, 2-buten-1-ol, crotyl alcohol, 1-penten-3-ol, trans-2-penten-1-ol, cis-2-penten-1-ol, 3-penten-2-ol, 4-penten-1-ol, 4-penten-2-ol, 1-hexen-3-ol, cis-2-hexen-1-ol, trans-2-hexen-1-ol, cis-3-hexen-1-ol, trans-3-hexen-1-ol, 4-hexen-1-ol, 5-hexen-1-ol, 5-hexen-2-ol, 1-hepten-3-ol, 1-octen-3-ol, trans-2-octen-1-ol, oleyl alcohol, terpene alcohol, propargyl alcohol and/or 2-butyne-1,4-diol.

Preferably, the reaction product obtained from alkylphosphonous acid derivatives (I) and diester-forming olefins (II) after step b) is reacted with a catalyst C, the reaction product being saponified.

Preferably, the catalyst C comprises Brönsted acids, Brönsted bases, water, mineral acids, sulfonic acids, alkali metal hydroxides and/or alkaline earth metal hydroxides.

The present invention also relates to the use of adducts formed from alkylphosphonous acid derivatives (I) and diester-forming olefins (II) according to one or more of claims 1 to 4 as an intermediate for further syntheses, as a binder, as a crosslinker or accelerant to cure epoxy resins, polyurethanes and unsaturated polyester resins, as polymer stabilizers, as crop protection agents, as a therapeutic or additive in therapeutics for humans and animals, as a sequestrant, as a mineral oil additive, as a corrosion control agent, in washing and cleaning applications and in electronics applications.

The present invention further relates to the use of adducts formed from alkylphosphonous acid derivatives (I) and diester-forming olefins (II) according to one or more of claims 1 to 4 as a flame retardant, more particularly a flame retardant for clearcoats and intumescent coatings, flame retardants for wood and other cellulose-containing products, as a reactive and/or nonreactive flame retardant for polymers, in the manufacture of flame-retardant polymeric molding compositions, in the manufacture of flame-retardant polymeric moldings and/or for flame-retardant finishing of polyester and cellulose straight and blend fabrics by impregnation.

The present invention also provides flame-retardant thermoplastic or thermoset polymeric molding composition comprising 0.5% to 45% by weight of adducts formed from alkylphosphonous acid derivatives (I) and diester-forming olefins (II) according to one or more of claims 1 to 4, 0.5% to 99% by weight of thermoplastic or thermoset polymer or mixtures thereof, 0% to 55% by weight of additives and 0% to 55% by weight of filler or reinforcing materials, wherein the sum total of the components is 100% by weight.

The invention lastly provides flame-retardant thermoplastic or thermoset polymeric moldings, films, threads and fibers comprising 0.5% to 45% by weight of adducts formed from alkylphosphonous acid derivatives (I) and diester-forming olefins (II) according to one or more of claims 1 to 4, 0.5% to 99% by weight of thermoplastic or thermoset polymer or mixtures thereof, 0% to 55% by weight of additives and 0% to 55% by weight of filler or reinforcing materials, wherein the sum total of the components is 100% by weight.

The process of the present invention comprises reacting
a) a phosphinic acid source with non-diester-forming olefins (III) in the presence of a catalyst A to form an alkylphosphonous acid derivative (I)
b) the resulting alkylphosphonous acid derivative (I) with diester-forming olefins (II) in the presence or absence of a catalyst B.

Another embodiment of the process of the present invention comprises reacting
a) a phosphinic acid source with non-diester-forming olefins (III) in the presence of a catalyst A to form an alkylphosphonous acid derivative (I),
b) the resulting alkylphosphonous acid derivative (I) with diester-forming olefins (II) in the presence or absence of a catalyst B, and
c) then with an ester former.

This process will later be called process 2.

A further embodiment of the process of the present invention comprises reacting
a) a phosphinic acid source with non-diester-forming olefins (III) in the presence of a catalyst A to form an alkylphosphonous acid derivative (I),
b) the resulting alkylphosphonous acid derivative (I) with diester-forming olefins (II) in the presence or absence of a catalyst B, and
c) then with a catalyst C, the product of step b) being saponified.

This process will later be called process 3.

Preferably, at the end of the aforementioned halogen-free processes of the present invention, the adducts obtained of alkylphosphonous acid derivatives (I) and diester-forming olefins (II), their acid, salt or ester can subsequently be reacted with metal compounds of Mg, Ca, Al, Sb, Sn, Ge, Ti, Fe, Zr, Zn, Ce, Bi, Sr, Mn, Li, Na, K and/or a protonated nitrogen base to form the corresponding adducts of alkylphosphonous acid derivatives (I) and diester-forming olefins (II) of these metals and/or of a nitrogen compound.

The alkylphosphonous esters preferably comprise alkyl, hydroxyalkyl, alkylaryl, aryl and/or alkenyl esters.

The esters more preferably comprise the methyl, ethyl, propyl, butyl, amyl, octyl, ethylhexyl, ethylene glycol, propylene glycol, butylene glycol, benzyl, phenyl, vinyl and/or allyl esters.

Useful diester-forming olefins (II) are of the type:

where $R^2$, $R^4$ are the same or different and represent $CO_2H$, $CO_2R^5$, $R^6$—$CO_2H$, $R^6$—$CO_2R^5$;

$R^1$, $R^3$ are the same or different and represent H, $R^5$; $R^5$ represents $C_1$-$C_{18}$-alkyl, $C_6$-$C_{18}$-aryl, $C_6$-$C_{18}$-arylalkyl, $C_6$-$C_{18}$-alkylaryl; $R^6$ represents $C_2$-$C_{18}$-alkylene, $C_6$-$C_{18}$-arylene, $C_6$-$C_{18}$-alkarylene and/or $C_6$-$C_{18}$-aralkylene.

Preferably, $R^1$, $R^4$ are also the same or different and represent $CO_2H$, $CO_2R^5$, $R^6$—$CO_2H$, $R^6$—$CO_2R^5$; $R^2$, $R^3$ are the same or different and represent H, $R^5$; $R^5$ represents $C_1$-$C_{18}$-alkyl, $C_6$-$C_{18}$-aryl, $C_6$-$C_{18}$-arylalkyl, $C_6$-$C_{18}$-alkylaryl; $R^6$ represents $C_2$-$C_{18}$-alkylene, $C_6$-$C_{18}$-arylene, $C_6$-$C_{18}$-alkarylene and/or $C_6$-$C_{18}$-aralkylene.

Preferably, $R^2$, $R^4$ are also the same or different and represent —CO—O—CO—, —CO—S—CO—, —CO-$NR^1$—CO—, —CO—$PR^1$—CO—; $R^1$, $R^3$ are the same or different and represent H, $R^5$; $R^5$ represents $C_1$-$C_{18}$-alkyl, $C_6$-$C_{18}$-aryl, $C_6$-$C_{18}$-arylalkyl, $C_6$-$C_{18}$-alkylaryl.

Preferably $R^1$, $R^2$ are also the same or different and represent $CO_2H$, CN, $CO_2R^5$, $R^6$—$CO_2H$, $R^6$—$CO_2R^5$; $R^3$, $R^4$ are the same or different and represent H, $R^5$; $R^5$ represents p0 $C_1$-$C_{18}$-alkyl, $C_6$-$C_{18}$-aryl, $C_6$-$C_{18}$-arylalkyl, $C_6$-$C_{18}$-alkylaryl; $R^6$ represents $C_2$-$C_{18}$-alkylene, $C_6$-$C_{18}$-arylene, $C_6$-$C_{18}$-alkarylene and/or $C_6$-$C_{18}$-aralkylene.

Preferably, $R^1$, $R^2$ are the same or different and represent —$CR_2^3$—CO—O—CO—, —$CR_2^3$—CO—$NR^1$—CO—, —$CR_2^3$—CO—O—CO—$CR_2^3$, —$CR_2^3$—CO—$NR^1$—CO—$CR_2^3$, $R^3$, $R^4$ are the same or different and represent H, $R^5$; $R^5$ represents $C_1$-$C_{18}$-alkyl, $C_6$-$C_{18}$-aryl, $C_6$-$C_{18}$-arylalkyl, $C_6$-$C_{18}$-alkylaryl.

Preferably, $R^2$ is =$R^4$ equal to —CO—$CR^5$=$CR^5$—CO—; $R^1$, $R^3$ are the same or different and represent H, $R^5$; $R^5$ represents $C_1$-$C_{18}$-alkyl, $C_6$-$C_{18}$-aryl, $C_6$-$C_{18}$-arylalkyl, $C_6$-$C_{18}$-alkylaryl.

Preferably, the diester-forming olefins (II) are also obtainable in situ and reactable with the alkylphosphonous acid derivative during their formation.

Step a) of the halogen-free processes of the present invention may comprise
a) reacting a phosphinic acid source with non-ester-forming olefins (III) in the presence of a catalyst A or of a catalyst system A,
b) optionally removing solvent and/or olefin,
c) removing catalyst A, catalyst system A, transition metal and/or transition metal compound,
d) removing ligands and/or complexing agent,
e) removing auxiliary and/or olefin.

Step a) of the halogen-free processes of the present invention may comprise reacting a phosphinic acid source with olefins in the presence of a catalyst A and filtering off insoluble product.

Step a) of the halogen-free processes of the present invention may also comprise
a) reacting a phosphinic acid source with non-ester-forming olefins (III) in the presence of a catalyst A,
b) optionally filtering off catalyst A,
c) removing ligands and/or complexing agent,
d) removing solvent,
e) recycling any removed catalyst or ligands and/or complexing agent into step a) to an extent of at least 90%.

It is particularly preferable for $R^7$, $R^8$, $R^9$, $R^{10}$ of olefin (III) to be the same or different and to represent independently H, methyl, ethyl, n-propyl, isopropyl, n-butyl, isobutyl, tert-butyl and/or phenyl.

Preference is also given to using functionalized olefins such as allyl isothiocyanate, allyl methacrylate, 2-allylphenol, N-allylthiourea, 2-(allylthio)-2-thiazoline, allyltrimethylsilane, allyl acetate, allyl acetoacetate, allyl alcohol, allylamine, allylbenzene, allyl cyanide, allyl cyanacetate, allylanisole, trans-2-pentenal, cis-2-pentenenitrile, 1-penten-3-ol, 4-penten-1-ol, 4-penten-2-ol, trans-2-hexenal, trans-2-hexen-1-ol, cis-3-hexen-1-ol, 5-hexen-1-ol, styrene, methylstyrene, 4-methylstyrene, vinyl acetate, 9-vinylanthracene, 2-vinylpyridine, 4-vinylpyridine and 1-vinyl-2-pyrrolidone.

It is particularly preferable for the olefins to comprise ethylene, 1-propylene, 1-butene, 1-pentene, 1-hexene and/or 1,3-butadiene.

Preferably, the transition metals for catalyst A comprise elements of the seventh and eighth transition groups (a metal of group 7, 8, 9 or 10, in modern nomenclature), for example rhenium, ruthenium, cobalt, rhodium, iridium, nickel, palladium and platinum.

Preference for use as source of the transition metals and transition metal compounds is given to their metal salts. Suitable salts are those of mineral acids containing the anions fluoride, chloride, bromide, iodide, fluorate, chlorate, bromate, iodate, fluorite, chlorite, bromite, iodite, hypofluorite, hypochlorite, hypobromite, hypoiodite, perfluorate, perchlorate, perbromate, periodate, cyanide, cyanate, nitrate, nitride, nitrite, oxide, hydroxide, borate, sulfate, sulfite, sulfide, persulfate, thiosulfate, sulfamate, phosphate, phosphite, hypophosphite, phosphide, carbonate and sulfonate, for example methanesulfonate, chlorosulfonate, fluorosulfonate, trifluoromethanesulfonate, benzenesulfonate, naphthylsulfonate, toluenesulfonate, t-butylsulfonate, 2-hydroxypropanesulfonate and sulfonated ion exchange resins; and/or organic salts, for example acetylacetonates and salts of a carboxylic acid having up to 20 carbon atoms, for example formate, acetate, propionate, butyrate, oxalate, stearate and citrate including halogenated carboxylic acids having up to 20 carbon atoms, for example trifluoroacetate, trichloroacetate.

A further source of the transition metals and transition metal compounds is salts of the transition metals with tetraphenylborate and halogenated tetraphenylborate anions, for example perfluorophenylborate.

Suitable salts similarly include double salts and complex salts consisting of one or more transition metal ions and independently one or more alkali metal, alkaline earth metal, ammonium, organic ammonium, phosphonium and organic phosphonium ions and independently one or more of the abovementioned anions. Examples of suitable double salts are ammonium hexachloropalladate and ammonium tetrachloropalladate.

Preference for use as a source of the transition metals is given to the transition metal as an element and/or a transition metal compound in its zerovalent state.

Preferably, the transition metal is used as a metal, or as an alloy with further metals, in which case boron, zirconium, tantalum, tungsten, rhenium, cobalt, iridium, nickel, palladium, platinum and/or gold is preferred here. The transition metal content in the alloy used is preferably 45-99.95% by weight.

Preferably, the transition metal is used in microdisperse form (particle size 0.1 mm-100 μm).

Preferably, the transition metal is used supported on a metal oxide such as, for example, alumina, silica, titanium dioxide, zirconium dioxide, zinc oxide, nickel oxide, vanadium oxide, chromium oxide, magnesium oxide, Celite®, diatomaceous earth, on a metal carbonate such as, for example, barium carbonate, calcium carbonate, strontium carbonate, on a metal sulfate such as, for example, barium sulfate, calcium sulfate, strontium sulfate, on a metal phosphate such as, for example, aluminum phosphate, vanadium phosphate, on a metal carbide such as, for example, silicone carbide, on a metal aluminate such as, for example, calcium aluminate, on a metal silicate such as, for example, aluminum silicate, chalks, zeolites, bentonite, montmorillonite, hectorite, on functionalized silicates, functionalized silica gels such as, for example, SiliaBond®, QuadraSil™, on functionalized polysiloxanes such as, for example, Deloxan®, on a metal nitride, on carbon, charcoal, mullite, bauxite, antimonite, scheelite, perovskite, hydrotalcite, heteropolyanions, on functionalized and unfunctionalized cellulose, chitosan, keratin, heteropolyanions, on ion exchangers such as, for example, Amberlite™, Amberjet™, Ambersep™, Dowex®, Lewatit®, ScavNet®, on functionalized polymers such as, for example, Chelex®, QuadraPure™, Smopex®, PolyOrgs®, on polymer-bound phosphanes, phosphane oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silica and/or dendrimers.

Suitable sources for the metal salts and/or transition metals likewise preferably include their complex compounds. Complex compounds of the metal salts and/or transition metals are composed of the metal salts/transition metals and one or more complexing agents. Suitable complexing agents include for example olefins, diolefins, nitriles, dinitriles, carbon monoxide, phosphines, diphosphines, phosphites, diphosphites, dibenzylideneacetone, cyclopentadienyl, indenyl or styrene. Suitable complex compounds of the metal salts and/or transition metals may be supported on the abovementioned support materials.

The proportion in which the supported transition metals mentioned are present is preferably in the range from 0.01% to 20% by weight, more preferably from 0.1% to 10% by weight and even more preferably from 0.2% to 5% by weight, based on the total mass of the support material.

Suitable sources for transition metals and transition metal compounds include for example palladium, platinum, nickel, rhodium; palladium, platinum, nickel or rhodium, on alumina, on silica, on barium carbonate, on barium sulfate, on calcium carbonate, on strontium carbonate, on carbon, on activated carbon; platinum-palladium-gold alloy, aluminum-nickel alloy, iron-nickel alloy, lanthanide-nickel alloy, zirconium-nickel alloy, platinum-iridium alloy, platinum-rhodium alloy; Raney® nickel, nickel-zinc-iron oxide; palladium(II) chloride, palladium(II) bromide, palladium(II) iodide, palladium(II) fluoride, palladium(II) hydride, palladium(II) oxide, palladium(II) peroxide, palladium(II) cyanide, palladium(II) sulfate, palladium(II) nitrate, palladium(II) phosphide, palladium(II) boride, palladium(II) chromium oxide, palladium(II) cobalt oxide, palladium(II) carbonate hydroxide, palladium(II) cyclohexane butyrate, palladium(II) hydroxide, palladium(II) molybdate, palladium(II) octanoate, palladium(II) oxalate, palladium(II) perchlorate, palladium(II) phthalocyanine, palladium(II) 5,9,14,18,23,27,32,36-octabutoxy-2,3-naphthalocyanine, palladium(II) sulfamate, palladium(II) perchlorate, palladium(II) thiocyanate, palladium(II) bis(2,2,6,6-tetramethyl-3,5-heptanedionate), palladium(II) propionate, palladium(II) acetate, palladium(II) stearate, palladium(II) 2-ethylhexanoate, palladium(II) acetylacetonate, palladium(II) hexafluoroacetylacetonate, palladium(II) tetrafluoroborate, palladium(II) thiosulfate, palladium(II) trifluoroacetate, palladium(II) phthalocyaninetetrasulfonic acid tetrasodium salt, palladium(II) methyl, palladium(II) cyclopentadienyl, palladium(II) methylcyclopentadienyl, palladium(II) ethylcyclopentadienyl, palladium(II) pentamethylcyclopentadienyl, palladium(II) 2,3,7,8,12,13,17,18-octaethyl-21H,23H-porphine, palladium(II) 5,10,15,20-tetraphenyl-21H,23H-porphine, palladium(II) bis(5-[[4-(dimethylamino)phenyl]imino]-8(5H)-quinolinone), palladium(II) 2,11,20,29-tetra-tert-butyl-2,3-naphthalocyanine, palladium(II) 2,9,16,23-tetraphenoxy-29H,31H-phthalocyanine, palladium(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenypimidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesitypimidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

nickel(II) chloride, nickel(II) bromide, nickel(II) iodide, nickel(II) fluoride, nickel(II) hydride, nickel(II) oxide, nickel(II) peroxide, nickel(II) cyanide, nickel(II) sulfate, nickel(II) nitrate, nickel(II) phosphide, nickel(II) boride, nickel(II) chromium oxide, nickel(II) cobalt oxide, nickel(II) carbonate hydroxide, nickel(II) cyclohexane butyrate, nickel(II) hydroxide, nickel(II) molybdate, nickel(II) octanoate, nickel(II) oxalate, nickel(II) perchlorate, nickel(II) phthalocyanine, nickel(II) 5,9,14,18,23,27,32,36-octabutoxy-2,3-naphthalocyanine, nickel(II) sulfamate, nickel(II) perchlorate, nickel(II) thiocyanate, nickel(II) bis(2,2,6,6-tetramethyl-3,5-heptanedionate), nickel(II) propionate, nickel(II) acetate, nickel(II) stearate, nickel(II) 2-ethylhexanoate, nickel(II) acetylacetonate, nickel(II) hexafluoroacetylacetonate, nickel(II) tetrafluoroborate, nickel(II) thiosulfate, nickel(II) trifluoroacetate, nickel(II) phthalocyaninetetrasulfonic acid tetrasodium salt, nickel(II) methyl, nickel(II) cyclopentadienyl, nickel(II) methylcyclopentadienyl, nickel(II) ethylcyclopentadienyl, nickel(II) pentamethylcyclopentadienyl, nickel(II) 2,3,7,8,12,13,17,18-octaethyl-21H,23H-porphine, nickel(II) 5,10,15,20-tetraphenyl-21H,23H-porphine, nickel(II) bis(5-[[4-(dimethylamino)phenyl]imino]-8(5H)-quinolinone), nickel(II) 2,11,20,29-tetra-tert-butyl-2,3-naphthalocyanine, nickel(II) 2,9,16,23-tetraphenoxy-29H,31H-phthalocyanine, nickel(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

platinum(II) chloride, platinum(II) bromide, platinum(II) iodide, platinum(II) fluoride, platinum(II) hydride, platinum(II) oxide, platinum(II) peroxide, platinum(II) cyanide, platinum(II) sulfate, platinum(II) nitrate, platinum(II) phosphide, platinum(II) boride, platinum(II) chromium oxide, platinum(II) cobalt oxide, platinum(II) carbonate hydroxide, platinum(II) cyclohexane butyrate, platinum(II) hydroxide, platinum(II) molybdate, platinum(II) octanoate, platinum(II) oxalate, platinum(II) perchlorate, platinum(II) phthalocyanine, platinum(II) 5,9,14,18,23,27,32,36-octabutoxy-2,3-naphthalocyanine, platinum(II) sulfamate, platinum(II) perchlorate, platinum(II) thiocyanate, platinum(II) bis(2,2,6,6-tetramethyl-3,5-heptanedionate), platinum(II) propionate, platinum(II) acetate, platinum(II) stearate, platinum(II) 2-ethylhexanoate, platinum(II) acetylacetonate, platinum(II) hexafluoroacetylacetonate, platinum(II) tetrafluoroborate, platinum(II) thiosulfate, platinum(II) trifluoroacetate, platinum(II) phthalocyaninetetrasulfonic acid tetrasodium salt, platinum(II) methyl, platinum(II) cyclopentadienyl, platinum(II) methylcyclopentadienyl, platinum(II) ethylcyclopentadienyl, platinum(II) pentamethylcyclopentadienyl, platinum(II) 2,3,7,8,12,13,17,18-octaethyl-21H,23H-porphine, platinum(II) 5,10,15,20-tetraphenyl-21H,23H-porphine, platinum(II) bis(5-[[4-(dimethylamino)phenyl]imino]-8(5H)-quinolinone), platinum(II) 2,11,20,29-tetra-tert-butyl-2,3-naphthalocyanine, platinum(II) 2,9,16,23-tetraphenoxy-29H,31H-phthalocyanine, platinum(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenyl-sulfinyl)ethane, 1,3-bis(2,6-diisopropylphenypimidazolidene)(3-chloropyridyl), 2'-(dimethylamino)-2-biphenylyl, dinorbornylphosphine, 2-(dimethylamino-methyl)ferrocene, allyl, bis(diphenylphosphino)butane, (N-succinimidyl)bis-(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

rhodium chloride, rhodium bromide, rhodium iodide, rhodium fluoride, rhodium hydride, rhodium oxide, rhodium peroxide, rhodium cyanide, rhodium sulfate, rhodium nitrate, rhodium phosphide, rhodium boride, rhodium chromium oxide, rhodium cobalt oxide, rhodium carbonate hydroxide, rhodium cyclohexane butyrate, rhodium hydroxide, rhodium molybdate, rhodium octanoate, rhodium oxalate, rhodium perchlorate, rhodium phthalocyanine, rhodium 5,9,14,18,23,27,32,36-octabutoxy-2,3-naphthalocyanine, rhodium sulfamate, rhodium perchlorate, rhodium thiocyanate, rhodium bis(2,2,6,6-tetramethyl-3,5-heptanedionate), rhodium propionate, rhodium acetate, rhodium stearate, rhodium 2-ethylhexanoate, rhodium acetylacetonate, rhodium hexafluoroacetylacetonate, rhodium tetrafluoroborate, rhodium thiosulfate, rhodium trifluoroacetate, rhodium phthalocyaninetetrasulfonic acid tetrasodium salt, rhodium methyl, rhodium cyclopentadienyl, rhodium methylcyclopentadienyl, rhodium ethylcyclopentadienyl, rhodium pentamethylcyclopentadienyl, rhodium 2,3,7,8,12,13,17,18-octaethyl-21H,23H-porphine, rhodium 5,10,15,20-tetraphenyl-21H,23H-porphine, rhodium bis(5[[4-(dimethylamino)phenyl]imino]-8(5H)-quinolinone), rhodium 2,11,20,29-tetra-tert-butyl-2,3-naphthalocyanine, rhodium 2,9,16,23-tetraphenoxy-29H,31H-phthalocyanine, rhodium 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenypimidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

potassium hexachloropalladate(IV), sodium hexachloropalladate(IV), ammonium hexachloropalladate(IV), potassium tetrachloropalladate(II), sodium tetrachloropalladate(II), ammonium tetrachloropalladate(II), bromo(tri-tert-butylphosphine)palladium(I) dimer, (2-methylallyl)palladium(II) chloride dimer, bis(dibenzylideneacetone)palladium(0), tris(dibenzylideneacetone)dipalladium(0), tetrakis(triphenylphosphine)palladium(0), tetrakis(tricyclohexylphosphine)-palladium(0), bis[1,2-bis(diphenylphosphino)ethane]palladium(0), bis(3,5,3',5'-dimethoxydibenzylideneacetone)palladium(0), bis(tri-tert-butylphosphine)palladium(0), meso-tetraphenyltetrabenzoporphinepalladium, tetrakis (methyldiphenylphosphine)palladium(0), tris(3,3',3"-phophinidyne-tris(benzenesulfonato)palladium(0) nonasodium salt, 1,3-bis(2,4,6-trimethylphenyl)imidazol-2-ylidene)(1,4-naphthoquinone)palladium(0), 1,3-bis(2,6-diisopropylphenyl)imidazol-2-ylidene(1,4-naphthoquinone)palladium(0) and the chloroform complex thereof;

allylnickel(II) chloride dimer, ammonionickel(II) sulfate, bis(1,5-cycloocta-diene)nickel(0), bis(triphenylphosphine) dicarbonylnickel(0), tetrakis(triphenyl-phosphine)nickel(0), tetrakis(triphenyl phosphite)nickel(0), potassium hexafluoronickelate(IV), potassium tetracyanonickelate(II), potassium nickel(IV) paraperiodate, dilithium tetrabromonickelate(II), potassium tetracyanonickelate(II);

platinum(IV) chloride, platinum(IV) oxide, platinum(IV) sulfide, potassium hexachloroplatinate(IV), sodium hexachloroplatinate(IV), ammonium hexachloroplatinate(IV), potassium tetrachloroplatinate(II), ammonium tetrachloroplatinate(II), potassium tetracyanoplatinate(II), trimethyl(methylcyclopentadienyl)platinum(IV), cis-diammintetrachloroplatinum(IV), potassium trichloro(ethylene)platinate(II), sodium hexahydroxyplatinate(IV), tetraamineplatinum(II) tetrachloroplatinate(II), tetrabutylammonium hexachloroplatinate(IV), ethylenebis(triphenylphosphine)platinum(0), platinum(0) 1,3-divinyl-1,1,3,3-tetramethyldisiloxane, platinum(0) 2,4,6,8-tetramethyl-2,4,6,8-tetravinylcyclotetrasiloxane, tetrakis(triphenylphosphine)platinum(0), platinum octaethylporphyrin, chloroplatinic acid, carboplatin;

chlorobis(ethylene)rhodium dimer, hexarhodium hexadecacarbonyl, chloro(1,5-cyclooctadiene)rhodium dimer, chloro(norbomadiene)rhodium dimer, chloro(1,5-hexadiene) rhodium dimer.

The ligands preferably comprise phosphines of the formula (IV)

$$PR^{11}{}_3 \qquad (IV)$$

where the $R^{11}$ radicals are each independently hydrogen, straight-chain, branched or cyclic $C_1$-$C_{20}$-alkyl, $C_6$-$C_{20}$-alkylaryl, $C_2$-$C_{20}$-alkenyl, $C_2$-$C_{20}$-alkynyl, $C_1$-$C_{20}$-carboxylate, $C_1$-$C_{20}$-alkoxy, $C_2$-$C_{20}$-alkenyloxy, $C_2$-$C_{20}$-alkynyloxy, $C_2$-$C_{20}$-alkoxycarbonyl, $C_1$-$C_{20}$-alkylsulfonyl, $C_1$-$C_{20}$-alkylsulfinyl, silyl and/or their derivatives and/or phenyl substituted by at least one $R^{12}$, or naphthyl substituted by at least one $R^{12}$. $R^{12}$ in each occurrence is independently hydrogen, fluorine, chlorine, bromine, iodine, $NH_2$, nitro, hydroxyl, cyano, formyl, straight-chain, branched or cyclic $C_1$-$C_{20}$-alkyl, $C_1$-$C_{20}$-alkoxy, $HN(C_1$-$C_{20}$-alkyl), $N(C_1$-$C_{20}$-alkyl)$_2$, —$CO_2$—($C_1$-$C_{20}$-alkyl), —$CON(C_1$-$C_{20}$-alkyl)$_2$, —$OCO$($C_1$-$C_{20}$-alkyl), $NHCO(C_1$-$C_{20}$-alkyl), $C_1$-$C_{20}$-acyl, —$SO_3M$, —$SO_2N(R^{10})M$, —$CO_2M$, —$PO_3M_2$, —$AsO_3M_2$, —$SiO_2M$, —$C(CF_3)_2OM$ (M=H, Li, Na or K), where $R^{13}$ is hydrogen, fluorine, chlorine, bromine, iodine, straight-chain, branched or cyclic $C_1$-$C_{20}$-alkyl, $C_2$-$C_{20}$-alkenyl, $C_2$-$C_{20}$-alkynyl, $C_1$-$C_{20}$-carboxylate, $C_1$-$C_{20}$-alkoxy, $C_2$-$C_{20}$-alkenyloxy, $C_2$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives, aryl, $C_6$-$C_{20}$-arylalkyl, $C_6$-$C_{20}$-alkylaryl, phenyl and/or biphenyl. Preferably, the $R^{11}$ groups are all identical.

Suitable phosphines (IV) are for example trimethylphosphine, triethylphosphine, tripropylphosphine, triisopropylphosphine, tributylphosphine, triisobutylphosphine, triisopentylphosphine, trihexylphosphine, tricyclohexylphosphine, trioctylphosphine, tridecylphosphine, triphenyiphosphine, diphenylmethylphosphine, phenyldimethylphosphine, tri(o-tolyl)phosphine, tri(p-tolyl) phosphine, ethyldiphenylphosphine, dicyclohexylphenylphosphine, 2-pyridyl-diphenylphosphine, bis(6-methyl-2-pyridyl)phenylphosphine, tri(p-chlorophenyl)-phosphine, tri(p-methoxyphenyl)phosphine, diphenyl(2-sulfonatophenyl)-phosphine; potassium, sodium and ammonium salts of diphenyl(3-sulfonatophenyl)phosphine, bis(4,6-dimethyl-3-sulfonatophenyl)(2,4-dimethylphenyl)phosphine, bis(3-sulfonatophenyl)phenylphosphines, tris(4,6-dimethyl-3-sulfonatophenyl)phosphines, tris(2-sulfonatophenyl)phosphines, tris(3-sulfonatophenyl) phosphines; 2-bis(diphenylphosphinoethyl) trimethylammonium iodide, 2'-dicyclohexylphosphino-2,6-dimethoxy-3-sulfonato-1,1-biphenyl sodium salt, trimethyl phosphite and/or triphenyl phosphite.

The ligands more preferably comprise bidentate ligands of the formula $$R^{11}M''\text{-}Z\text{-}M''R^{11} \qquad (V).$$

In this formula, each M" independently is N, P, As or Sb.
M" is preferably the same in the two occurrences and more preferably is a phosphorus atom.

Each $R^{11}$ group independently represents the radicals described under formula (VI). The $R^{11}$ groups are preferably all identical.

Z is preferably a bivalent bridging group which contains at least 1 bridging atom, preferably from 2 to 6 bridging atoms.

Bridging atoms can be selected from carbon, nitrogen, oxygen, silicon and sulfur atoms. Z is preferably an organic bridging group containing at least one carbon atom. Z is preferably an organic bridging group containing 1 to 6 bridging atoms, of which at least two are carbon atoms, which may be substituted or unsubstituted.

Preferred Z groups are —$CH_2$—, —$CH_2$—$CH_2$—, —$CH_2$—$CH_2$—$CH_2$—, —$CH_2$—$CH(CH_3)$—$CH_2$—, —$CH_2$—$C(CH_3)_2$—$CH_2$—, —$CH_2$—$C(C_2H_5)$—$CH_2$—, —$CH_2$—$Si(CH_3)_2$—$CH_2$—, —$CH_2$—O—$CH_2$—, —$CH_2$—$CH_2$—$CH_2$—$CH_2$—, —$CH_2$—$CH(C_2H_5)$—$CH_2$—, —$CH_2$—$CH(n\text{-}Pr)$—$CH$ and —$CH_2$—$CH(n\text{-}Bu)$-$CH_2$—, substituted or unsubstituted 1,2-phenyl, 1,2-cyclohexyl, 1,1'- or 1,2-ferrocenyl radicals, 2,2'-(1,1'-biphenyl), 4,5-xanthene and/or oxydi-2,1-phenylene radicals.

Examples of suitable bidentate phosphine ligands (V) are 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino) ethane, 1,2-bis(di-tert-butylphosphino)ethane, 1,2-bis (dicyclohexylphosphino)ethane, 1,2-bis (diphenylphosphino)ethane; 1,3-bis (dicyclohexylphosphino)propane, 1,3-bis (diisopropylphosphino)propane, 1,3-bis(di-tert-butylphosphino)propane, 1,3-bis(diphenylphosphino) propane; 1,4-bis(diisopropylphosphino)butane, 1,4-bis (diphenylphosphino)butane; 1,5-bis (dicyclohexylphosphino)pentane; 1,2-bis(di-tert-butylphosphino)benzene, 1,2-bis(diphenylphosphino) benzene, 1,2-bis(dicyclohexylphosphino)benzene, 1,2-bis (dicyclopentylphosphino)benzene, 1,3-bis(di-tert-butylphosphino)benzene, 1,3-bis(diphenylphosphino) benzene, 1,3-bis(dicyclohexylphosphino)benzene, 1,3-bis (dicyclopentylphosphino)benzene; 9,9-dimethyl-4,5-bis (diphenylphosphino)-xanthene, 9,9-dimethyl-4,5-bis (diphenylphosphino)-2,7-di-tert-butylxanthene, 9,9-dimethyl-4,5-bis(di-tert-butylphosphino)xanthene, 1,1'-bis (diphenylphosphino)-ferrocene, 2,2'-bis (diphenylphosphino)-1,1'-binaphthyl, 2,2'-bis(di-p-tolylphosphino)-1,1'-binaphthyl, (oxydi-2,1-phenylene)bis (diphenylphosphine), 2,5-(diisopropylphospholano)

benzene, 2,3-O-isopropylidene-2,3-dihydroxy-1,4-bis (diphenylphosphino)butane, 2,2'-bis(di-tert-butylphosphino)-1,1'-biphenyl, 2,2'-bis(dicyclohexylphosphino)-1,1'-biphenyl, 2,2'-bis(diphenylphosphino)-1,1'-biphenyl, 2-(di-tert-butylphosphino)-2'-(N,N-dimethylamino)biphenyl, 2-(dicyclohexylphosphino)-2'-(N,N-dimethylamino)biphenyl, 2-(diphenylphos-phino)-2'-(N,N-dimethylamino)biphenyl, 2-(diphenylphosphino)ethylamine, 2-[2-(diphenylphosphino)ethyl]pyridine; potassium, sodium and ammonium salts of 1,2-bis(di-4-sulfonatophenylphosphino)benzene, (2,2'-bis[[bis(3-sulfonato-phenyl)phosphino]methyl]-4,4',7,7'-tetrasulfonato-1,1'-binaphthyl, (2,2'-bis[[bis(3-sulfonatophenyl)phosphino]methyl]-5,5'-tetrasulfonato-1,1'-biphenyl, (2,2'-bis[[bis(3-sulfonatophenyl)phosphino]methyl]-1,1'-binaphthyl, (2,2'-bis[[bis(3-sulfonatophenyl)phosphino]methyl]-1,1'-biphenyl, 9,9-dimethyl-4,5-bis(diphenylphosphino)-2,7-sulfonatoxanthene, 9,9-dimethyl-4,5-bis(di-tert-butylphosphino)-2,7-sulfonatoxanthene, 1,2-bis(di-4-sulfonatophenylphosphino)-benzene, meso-tetrakis(4-sulfonatophenyl)porphine, meso-tetrakis(2,6-dichloro-3-sulfonatophenyl)porphine, meso-tetrakis(3-sulfonatomesityl)porphine, tetrakis(4-carboxyphenyl)porphine and 5,11,17,23-sulfonato-25,26,27,28-tetrahydroxycalix[4]arene.

Moreover, the ligands of the formula (IV) and (V) can be attached to a suitable polymer or inorganic substrate by the $R^{11}$ radicals and/or the bridging group.

The molar transition metal/ligand ratio of the catalyst system is in the range from 1:0.01 to 1:100, preferably in the range from 1:0.05 to 1:10 and more preferably in the range from 1:1 to 1:4.

The reactions in the process stages a), b) and c) preferably take place, if desired, in an atmosphere comprising further gaseous constituents such as nitrogen, oxygen, argon, carbon dioxide for example; the temperature is in the range from −20 to 340° C., more particularly in the range from 20 to 180° C., and total pressure is in the range from 1 to 100 bar.

The products and/or the component and/or the transition metal and/or the transition metal compound and/or catalyst system and/or the ligand and/or starting materials are optionally isolated after the process stages a), b) and c) by distillation or rectification, by crystallization or precipitation, by filtration or centrifugation, by adsorption or chromatography or other known methods.

According to the present invention, solvents, auxiliaries and any other volatile constituents are removed by distillation, filtration and/or extraction for example.

The reactions in the process stages a), b) and c) are preferably carried out, if desired, in absorption columns, spray towers, bubble columns, stirred tanks, trickle bed reactors, flow tubes, loop reactors and/or kneaders.

Suitable mixing elements include for example anchor, blade, MIG, propeller, impeller and turbine stirrers, cross beaters, disperser disks, hollow (sparging) stirrers, rotor-stator mixers, static mixers, Venturi nozzles and/or mammoth pumps.

The intensity of mixing experienced by the reaction solutions/mixtures preferably corresponds to a rotation Reynolds number in the range from 1 to 1 000 000 and preferably in the range from 100 to 100 000.

It is preferable for an intensive commixing of the respective reactants etc. to be effected by an energy input in the range from 0.080 to 10 kW/m$^3$, preferably 0.30-1.65 kW/m$^3$.

During the reaction, the catalyst A is preferably homogeneous and/or heterogeneous in action. Therefore, the particular heterogeneous catalyst acts during the reaction as a suspension or bound to a solid phase.

Preferably, the catalyst A is generated in situ before the reaction and/or at he start of the reaction and/or during the reaction.

Preferably, the particular reaction takes place in a solvent as a single-phase system in homogeneous or heterogeneous mixture and/or in the gas phase.

When a multi-phase system is used, a phase transfer catalyst may be used in addition.

The reactions of the present invention can be carried out in liquid phase, in the gas phase or else in supercritical phase. The catalyst A is preferably used in the case of liquids in homogeneous form or as a suspension, while a fixed bed arrangement is advantageous in the case of gas phase or supercritical operation.

Suitable solvents are water, alcohols, e.g. methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc. Preference is further given to glycols, e.g. ethylene glycol, 1,2-propanediol, 1,3-propanediol, 1,3-butanediol, 1,4-butanediol, diethylene glycol etc.; aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloroethane, chlorobenzene, carbon tetrachloride, tetrabromoethylene, etc.; alicyclic hydrocarbons, such as cyclopentane, cyclohexane, and methylcyclohexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone etc.; esters, such as methyl formate, methyl acetate, ethyl acetate, n-propyl acetate, and n-butyl acetate, etc.; carboxylic acids, such as formic acid, acetic acid, propionic acid, butyric acid, etc. One or more of these compounds can be used, alone or in combination.

Suitable solvents also encompass the phosphinic acid sources and olefins used. These have advantages in the form of higher space-time yield.

It is preferable that the reaction be carried out under the autogenous vapor pressure of the olefin and/or of the solvent.

The partial pressure of the olefin during the reaction is preferably 0.01-100 bar and more preferably 0.1-10 bar.

The phosphinic acid/olefin molar ratio for the reaction is preferably in the range from 1:10 000 to 1:0.001 and more preferably in the range from 1:30 to 1:0.01.

The phosphinic acid/catalyst molar ratio for the reaction is preferably in the range from 1:1 to 1:0.00000001 and more preferably in the range from 1:0.01 to 1:0.000001.

The phosphinic acid/solvent molar ratio for the reaction is preferably in the range from 1:10 000 to 1:0 and more preferably in the range from 1:50 to 1:1.

One present invention process for preparing alkylphosphonous acids and their derivatives (I) comprises reacting a phosphinic acid source with olefins in the presence of a catalyst and freeing the product (I) (alkylphosphonous acid, salts or esters) of catalyst, transition metal or transition metal compound, ligand, complexing agent, salts and by-products.

The present invention provides that the catalyst, the catalyst system, the transition metal and/or the transition metal compound are separated off by adding an auxiliary 1 and removing the catalyst, the catalyst system, the transition metal and/or the transition metal compound by extraction and/or filtration.

The present invention provides that the ligand and/or complexing agent is separated off by extraction with auxiliary 2 and/or distillation with auxiliary 2.

Auxiliary 1 is preferably water and/or at least one member of the group of metal scavengers. Preferred metal scavengers are metal oxides, such as aluminum oxide, silicon dioxide, titanium dioxide, zirconium dioxide, zinc oxide, nickel oxide, vanadium oxide, chromium oxide, magnesium oxide, Celite®, kieselguhr; metal carbonates, such as barium carbonate, calcium carbonate, strontium carbonate; metal sulfates, such as barium sulfate, calcium sulfate, strontium sulfate; metal phosphates, such as aluminum phosphate, vanadium phosphate, metal carbides, such as silicone carbide; metal aluminates, such as calcium aluminate; metal silicates, such as aluminum silicate, chalks, zeolites, bentonite, montmorillonite, hectorite; functionalized silicates, functionalized silica gels, such as SiliaBond®, QuadraSil™; functionalized polysiloxanes, such as Deloxan®; metal nitrides, carbon, activated carbon, mullite, bauxite, antimonite, scheelite, perovskite, hydrotalcite, functionalized and unfunctionalized cellulose, chitosan, keratin, heteropolyanions, ion exchangers, such as Amberlite™, Amberjet™, Ambersep™, Dowex®, Lewatit®, ScavNet®; functionalized polymers, such as Chelex®, QuadraPure™, Smopex®, Poly-Orgs®; polymer-bound phosphanes, phosphane oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silicon dioxide, and/or dendrimers.

It is preferable that the amounts added of auxiliary 1 correspond to 0.1-40% by weight loading of the metal on auxiliary 1.

It is preferable that auxiliary 1 be used at temperatures of from 20 to 90° C.

It is preferable that the residence time of auxiliary 1 be from 0.5 to 360 minutes.

Auxiliary 2 is preferably the aforementioned solvent of the present invention as are preferably used in process stage a).

Preferably, step b) of the processes of the present invention is carried out in the presence of a catalyst B. Preference is given to Brönsted acids, bases, free-radical initiators and photoinitiators.

Preferred bases are organic bases and/or organometal bases.

Preferred organometal bases are alkoxides of the $1^{st}$ and $2^{nd}$ main groups and of the $4^{th}$ transition group. Particular preference is given to sodium methoxide, sodium ethoxide, sodium butoxide, potassium methoxide, potassium ethoxide, potassium butoxide, titanium(IV) propoxide and/or titanium (IV) butoxide.

Preferred catalysts B are also metals, metal hydrides such as, for example, lithium, lithium hydride, lithium aluminohydride, methyllithium, butyllithium, tert-butyllithium, lithium diisopropylamide, sodium, sodium hydride, sodium borohydride.

Preferred free-radical initiators for step b) are peroxo compounds such as peroxomonosulfuric acid, potassium persulfate (potassium peroxomonosulfate), Caroat™, Oxone™, peroxodisulfuric acid, potassium persulfate (potassium peroxodisulfate), sodium persulfate (sodium peroxodisulfate), ammonium persulfate (ammonium peroxodisulfate).

Particular preference is given to compounds capable of forming peroxides in the solvent system of step b), such as sodium peroxide, sodium peroxide diperoxohydrate, sodium peroxide diperoxohydratehydrate, sodium peroxide dihydrate, sodium peroxide octahydrate, lithium peroxide, lithium peroxide monoperoxohydratetrihydrate, calcium peroxide, strontium peroxide, barium peroxide, magnesium peroxide, zinc peroxide, potassium hyperoxide, potassium peroxide diperoxohydrate, sodium peroxoborate tetrahydrate, sodium peroxoborate trihydrate, sodium peroxoborate monohydrate, anhydrous sodium peroxoborate, potassium peroxoborate peroxohydrate, magnesium peroxoborate, calcium peroxoborate, barium peroxoborate, strontium peroxoborate, potassium peroxoborate, peroxomonophosphoric acid, peroxodiphosphoric acid, potassium peroxodiphosphate, ammonium peroxodiphosphate, potassium ammonium peroxodiphosphates (double salt), sodium carbonate peroxohydrate, urea peroxohydrate, ammonium oxalate peroxide, barium peroxide peroxohydrate, barium peroxide peroxohydrate, calcium hydrogen peroxides, calcium peroxide peroxohydrate, ammonium triphosphate diperoxophosphate hydrate, potassium fluoride peroxohydrate, potassium fluoride triperoxohydrate, potassium fluoride diperoxohydrate, sodium pyrophosphate diperoxohydrate, sodium pyrophosphate diperoxohydrate octahydrate, potassium acetate peroxohydrate, sodium phosphate peroxohydrate, sodium silicate peroxohydrate.

Preferred catalysts B are hydrogen peroxide, performic acid, peracetic acid, benzoyl peroxide, di-t-butyl peroxide, dicumyl peroxide, 2,4-dichlorobenzoyl peroxide, decanoyl peroxide, lauryl peroxide, cumene hydroperoxide, pinene hydroperoxide, p-menthane hydroperoxide, t-butyl hydroperoxide, acetylacetone peroxide, methyl ethyl ketone peroxide, succinic acid peroxide, dicetyl peroxydicarbonate, t-butyl peroxyacetate, t-butylperoxymaleic acid, t-butyl peroxybenzoate, acetyl cyclohexylsulfonyl peroxide.

Water-soluble azo initiators are preferably used as free-radical initiators for step b). Preference is given to azo initiators such as VAZO® 52 2,2'-azobis(2,4-dimethylvaleronitrile), VAZO® 64 (azobis(isobutyronitrile), AIBN), VAZO® 67 2,2'-azobis(2-methylbutyronitrile), VAZO® 88 1,1'-azobis(cyclohexane-1-carbonitrile), VAZO® 68 from Dupont-Biesteritz, V-70 2,2'-azobis(4-methoxy-2,4-dimethylvaleronitrile), V-65 2,2'-azobis(2,4-dimethylvaleronitrile), V-601 dimethyl 2,2'-azobis(2-methylpropionate), V-59 2,2'-azobis (2-methylbutyronitrile), V-40 1,1'-azobis(cyclohexane-1-carbonitrile), VF-096 2,2'-azobis[N-(2-propenyl)-2-methylpropionamide], V-30 1-[(cyano-1-methylethyl)azo] formamide, VAm-110 2,2'-azobis(N-butyl-2-methylpropionamide), VAm-111 2,2'-azobis(N-cyclohexyl-2-methylpropionamide), VA-046B 2,2'-azobis[2-(2-imidazolin-2-yl)propane disulfate dihydrate, VA-057 2,2'-azobis[N-(2-carboxyethyl)-2-methylpropionamidine] tetrahydrate, VA-061 2,2'-azobis[2-(2-imidazolin-2-yl) propane], VA-080 2,2'-azobis{2-methyl-N-[1,1-bis (hydroxymethyl)-2-hydroxyethyl]propionamide, VA-085 2,2'-azobis{2-methyl-N-[2-(1-hydroxybutyl)]propionamide}, VA-086 2,2'-azobis[2-methyl-N-(2-hydroxyethyl) propionamide] from Wako Chemicals.

It is also possible to use azo initiators such as 2-tert-butylazo-2-cyanopropane, dimethyl azodiisobutyrate, azodiisobutyronitrile, 2-tert-butylazo-1-cyano-cyclohexane, 1-tert-amylazo-1-cyanocyclohexane. Preference is further given to alkyl perketals such as 2,2-bis(tert-butylperoxy)butane, ethyl 3,3-bis(tert-butylperoxy)butyrate, 1,1-di(tert-butylperoxy)cyclohexane.

The ratio of catalyst B to alkylphosphonous acid derivative in step b) is preferably in the range from 1:100 to 100:1 and more preferably in the range from 1:50 to 1:1.

The ratio of solvent to alkylphosphonous acid derivative in step b) is preferably in the range from 1:1000 to 50:1.

The initiator B is preferably metered in at a rate of 0.01 to 10 mol % of catalyst per hour, based on the phosphorus-containing compound.

The reaction in step b) is preferably carried out under the autogenous vapor pressure of the diester-forming olefin (II) and/or of the solvent.

Suitable solvents are the solvents mentioned for step a).

The reaction in step b) is preferably carried out at a partial pressure of the diester-forming olefin of 0.01-100 bar.

The reaction in step b) is preferably carried out at a temperature of from 0 to 250° C., more preferably at a temperature of 20 to 200° C. and more particularly at a temperature of 50 to 150° C.

The reaction in step b) is preferably carried out at a total pressure of 1 to 100 bar.

The present invention further provides a process for continuous preparation of adducts of alkylphosphonous acid derivatives (I) and diester-forming olefins (II) by reaction of alkylphosphonous esters (I) with ester-forming olefins in the presence of metal alkoxides (catalyst B), which process comprises a) initially charging a self-contained reactor configured to recirculate the reaction mixture and equipped with cooling means and also an overflow with a volume corresponding to the reactor volume of the adduct to be prepared from alkylphosphonous acid derivative and diester-forming olefin, optionally in admixture with alcohol corresponding to the metal alkoxide as solvent, and recirculating, b) the alkylphosphonous ester (I), ester-forming olefin (II) and also an alcoholic solution of the metal alkoxide being continuously introduced into the reactor with cooling of the recirculated reactor contents and reacted at a temperature of about 0 to 80° C. in the course of about 5-120 minutes, wherein the molar ratio of the alkylphosphonous ester (I) to the ester-forming olefin (II) is about 1:0.9-2 and the amount of the metal alkoxide, based on the alkylphosphonous ester (I), is about 0.1 to 5 mol %, and c) continuously withdrawing, over the overflow of the reactor, a mixture comprising the reaction product and separating the adduct of alkylphosphonous acid derivative and diester-forming olefin from the mixture.

In a preferred embodiment of the process according to the present invention, the reaction of the reaction components is carried out at a temperature of 20 to 50° C. The charging of the reactor with the reaction components and the catalyst solution can be carried out for example by a) passing the alkylphosphonous ester (I), the ester-forming olefin (II) and also the alcoholic solution of the metal alkoxide into the reactor separately, b) passing a mixture of the alkylphosphonous ester (I) with the ester-forming olefin (II) into the reactor separately from the alcoholic solution of the metal alkoxide, or c) passing a mixture of the alkylphosphonous ester (I) with the alcoholic solution of the metal alkoxide into the reactor separately from the ester-forming olefin (II).

The ester radicals of the alkylphosphonous ester (I) and of the ester-forming olefin (II) may be the same or different. It is further advantageous when the alcohol used as solvent and/or the alcoholic component of the metal alkoxide corresponds either to the alcoholic component of the alkylphosphonous ester (I) and/or to that of the ester-forming olefin (II).

Lastly, preferred features of the invention consist in the molar ratio of alkylphosphonous ester (I) to ester-forming olefin (II) being in the range of 1:1-1.3, the amount of catalyst B based on the alkylphosphonous ester (I) being 1-5 mol % and the amount of alcohol used as solvent being 0.1-1000 mol per mole of alkylphosphonous ester (I).

When alkylphosphonous ester (I) and ester-forming olefin (II) are used with different ester radicals and also an alcoholic metal alkoxide solution corresponding to these ester radicals is used, a mixed product is obtained.

The method of the present invention makes it possible to produce adducts of alkylphosphonous acid derivative and diester-forming olefin continuously on an industrial scale in a hitherto unattained yield of about 95% of theory.

The volatile components are preferably removed in step b) in vacuo at 0.01 to 1 bar.

Preference is given to using the present invention adducts of alkylphosphonous acid derivatives (I) and diester-forming olefins (II)

as binders e.g. for foundry materials and molding sands;
as crosslinkers or accelerants in the curing of epoxy resins, polyurethanes, unsaturated polyester resins;
as polymer stabilizers, e.g., as light stabilizer and/or heat stabilizer for cotton fabrics, polymeric fibers, plastics;
as crop protection agent, e.g. as plant growth regulator, as herbicide, herbicide, pesticide, (soil) fungicide;
as a diagnostic, therapeutic or additive in therapeutics for humans and animals, e.g. as enzyme modulator, for stimulating tissue growth;
as sequestrant e.g. for scale control in industrial water-ducting systems, in petroleum production and in metal-treating agents;
as petroleum additive e.g. as antioxidant and for enhancing the octane number;
as corrosion control agent;
in washing and cleaning applications, e.g. as decolorizer;
in electronics applications, e.g. in polyelectrolytes for capacitors, primary batteries and secondary batteries, and also as free-radical scavenger in photosensitive layers;
as polymerization catalyst for polyester;
copolycondensable flame retardant for polyester and polyamide fibers;
polyester masterbatch;
heat and light stabilizer for polymers;
as intermediates for angiotensin-converting enzyme inhibitors;
as alanylaminopeptidase inhibitors for cell functional control and treatment of immunological, inflammatory, neuronal and other disorders or as intermediates in the manufacture thereof;
as dipeptidylpeptidase IV inhibitor or as intermediate in its manufacture;
as inhibitors for epoxide hydrolase for treating high blood pressure or as intermediate in the manufacture thereof;
for fiber pretreatment and surface modification.

Preference is given to the use of the present invention adducts of alkylphosphonous acid derivatives (I) and diester-forming olefins (II) for producing esters (and polyesters) by esterification in step c) of process 2 when either in formula (I) X is =H or in formula (II) $R^2$, $R^4$ or $R^1$, $R^4$ or $R^1$, $R^2$ are the same or different and are at least one representative from the group consisting of $CO_2H$, $R^6$—$CO_2H$; or $R^2$ and $R^4$ are the same and are at least one representative from the group consisting of —CO—O—CO—, —CO—S—CO—, —O—NR$^1$—CO—, —CO—PR$^1$—CO—; or R$^1$, R$^2$ are the same and are at least one representative from the group consisting of —CR$_2^3$—CO—O—CO—, —CR$_2^3$—CO—NR$^1$—CO—, —CR$_2^3$—CO—O—CO—CR$_2^3$, —CR$_2^3$—CO—NR$^1$—CO—CR$_2^3$;

R$^1$, R$^3$ or R$^2$, R$^3$ or R$^3$, R$^4$ are the same or different and represent at least one representative from the group consisting of H, R$^5$, R$^5$ represents C$_1$-C$_{18}$-alkyl, C$_6$-C$_{18}$-aryl, C$_6$-C$_{18}$-arylalkyl, C$_6$-C$_{18}$-alkylaryl;

R$^6$ represents C$_2$-C$_{18}$-alkylene, C$_6$-C$_{18}$-arylene, C$_6$-C$_{18}$-alkarylene and/or C$_6$-C$_{18}$-aralkylene.

It is preferable according to the present invention for step c) of process 2 to comprise adducts formed from alkylphosphonous acid derivatives (I) and diester-forming olefin moiety which bear an unesterified phosphinic acid function on the alkylphosphonous acid moiety being esterified in this way by reaction with an ester former.

It is preferable according to the present invention for step c) of process 2 to comprise adducts formed from alkylphosphonous acid derivatives (I) and diester-forming olefin moiety which bear an unesterified carboxylic acid function on the diester-forming olefin moiety being esterified in this way by reaction with an ester former.

It is preferable according to the present invention for step c) of process 2 to comprise adducts formed from alkylphosphonous acid derivatives (I) and diester-forming olefin moiety which bear an ester function on the alkylphosphonous acid moiety being transesterified in this way by reaction with an ester former.

It is preferable according to the present invention for step c) of process 2 to comprise adducts formed from alkylphosphonous acid derivatives (I) and diester-forming olefin moiety which bear an ester function on the carboxylic acid moiety being transesterified in this way by reaction with an ester former.

Ester formers suitable according to the present invention are C$_1$-C$_{20}$ saturated and unsaturated mono-, di-, tri- and tetrahydric alcohols, more preferably C$_1$-C$_8$ saturated and unsaturated mono-, di-, tri- and tetrahydric alcohols and most preferably methanol, ethanol, propanol, butanol, amyl alcohol, octanol, ethylene glycol, polyethyleneglycol, 1,2-propanediol, 1,3-propanediol, butanediol, glycerol, erythritol, pentaerythritol, allyl alcohol, 3-buten-1-ol, 3-hydroxy-1-butene, 3-buten-2-ol, methylvinylcarbinol, 2-methyl-2-propen-1-ol, methallyl alcohol, 2-buten-1-ol, crotyl alcohol, 1-penten-3-ol, trans-2-penten-1-ol, cis-2-penten-1-ol, 3-penten-2-ol, 4-penten-1-ol, 4-penten-2-ol, 1-hexen-3-ol, cis-2-hexen-1-ol, trans-2-hexen-1-ol, cis-3-hexen-1-ol, trans-3-hexen-1-ol, 4-hexen-1-ol, 5-hexen-1-ol, 5-hexen-2-ol, 1-hepten-3-ol, 1-octen-3-ol, trans-2-octen-1-ol, oleyl alcohol, terpene alcohol, propargyl alcohol and/or 2-butyne-1,4-diol.

Preference is given to using the present invention adducts of alkylphosphonous acid derivatives and diester-forming olefins for producing acids by saponification in step c) of process 3 when either in formula I X represents H, C$_1$-C$_{18}$-alkyl, C$_6$-C$_{18}$-aryl, C$_6$-C$_{18}$-arylalkyl, C$_6$-C$_{18}$-alkylaryl, C$_2$-C$_{18}$-alkylene or in formula (II) R$^2$, R$^4$ or R$^1$, R$^4$ or R$^1$, R$^2$ are the same or different and are at least one representative from the group consisting of CO$_2$H, R$^6$—CO$_2$H; or R$^2$ and R$^4$ are the same and are at least one representative from the group consisting of —CO—O—CO—, —CO—S—CO—, —O—NR$^1$—CO—, —CO—PR$^1$—CO—; or R$^1$, R$^2$ are the same and are at least one representative from the group consisting of —CR$_2^3$—CO—O—CO—, —CR$_2^3$—CO—NR$^1$—CO—, —CR$_2^3$—CO—O—CO—CR$_2^3$, —CR$_2^3$—CO—NR$^1$—CO—CR$_2^3$; R$^1$, R$^3$ or R$^2$, R$^3$ or R$^3$, R$^4$ are the same or different and represent at least one representative from the group consisting of H, R$^5$;

R$^5$ represents C$_1$-C$_{18}$-alkyl, C$_6$-C$_{18}$-aryl, C$_6$-C$_{18}$-arylalkyl, C$_6$-C$_{18}$-alkylaryl;

R$^6$ represents C$_2$-C$_{18}$-alkylene, C$_6$-C$_{18}$-arylene, C$_8$-C$_{18}$-alkarylene and/or C$_6$-C$_{18}$-aralkylene.

It is preferable according to the present invention for step c) of process 3 to comprise adducts formed from alkylphosphonous acid derivatives (I) and diester-forming olefin moiety which bear an ester function on the alkylphosphonous acid moiety being saponified in this way by reaction with a catalyst C to the phosphinic acid function.

It is preferable according to the present invention for step c) of process 3 to comprise adducts formed from alkylphosphonous acid derivatives (I) and diester-forming olefin moiety which bear an ester function on the carboxylic acid moiety being saponified in this way by reaction with a catalyst C to the carboxylic acid function.

It is preferable according to the present invention for step c) of process 3 to comprise adducts formed from alkylphosphonous acid derivatives (I) and diester-forming olefin moiety which bear at least one nitrile function on the carboxylic acid moiety being saponified in this way by reaction with a catalyst C to the carboxylic acid function.

Catalysts C preferred according to the present invention are Brönsted acids, Brönsted bases, water, preferably mineral acids such as for example hydrochloric acid, sulfuric acid, nitric acid, phosphoric acid, sulfonic acids, alkali metal hydroxides or alkaline earth metal hydroxides.

Suitable bases are metals, metal hydrides and metal alkoxides such as for example lithium, lithium hydride, lithium aluminohydride, methyllithium, butyllithium, t-butyllithium, lithium diisopropylamide, sodium, sodium hydride, sodium borohydride, sodium methoxide, sodium ethoxide, sodium butoxide, potassium methoxide, potassium ethoxide and potassium butoxide and also sodium hydroxide, potassium hydroxide, lithium hydroxide and barium hydroxide.

Very particular preference is given to using sulfuric acid, hydrochloric acid, phosphoric acid, toluenesulfonic acid, aqueous sodium hydroxide solution, aqueous potassium hydroxide solution, calcium hydroxide solution.

When a salt of an adduct of an alkylphosphonous acid (I) and a diester-forming olefin (II) is obtained, it may be reacted with a mineral acid to form the corresponding acid and esterified similarly to step b).

When an ammonium salt of an adduct of an alkylphosphonous acid and a diester-forming olefin is obtained, it may initially be reacted with a base to form a salt of an adduct of an alkylphosphonous acid and a diester-forming olefin, which salt is then reacted with a mineral acid to form the corresponding acid and esterified similarly to step b).

The acidic or alkaline hydrolysis may preferably be carried out in the presence of water and an inert solvent. Suitable inert solvents are the solvents mentioned in process step a), preference being given to low molecular weight alcohols having 1 to 6 carbon atoms.

The presence of water is essential to performing the hydrolysis. The amount of water may range from the stoichiometric requirements as a minimum up to an excess.

The hydrolysis is preferably carried out in a phosphorus/water molar ratio of 1:1 to 1:1000 and more preferably 1:1 to 1:10.

The hydrolysis is preferably carried out in a phosphorus/base or acid molar ratio of 1:1 to 1:300 and more preferably 1.1 to 1:20.

The amount of solvent used ranges from 0.5 kg to 1.5 kg per kg of the adducts of alkylphosphonous acid derivative (I) and diester-forming olefin (II), preferably from 0.6 kg to 1.0 kg.

The reaction temperature is preferably 50° C. to 140° C., preferably from 80° C. to 130° C.

The reaction is preferably carried out at a total pressure of 1 to 100 bar, particular preference being given to a total pressure of 1 to 10 bar.

The reaction time is 0.2 to 20 hours, preferably 1 to 12 hours.

The adducts of alkylphosphonous acid derivative (I) and diester-forming olefin (II) can subsequently be converted into further metal salts.

The metal compounds used preferably comprise compounds of the metals Mg, Ca, Al, Sb, Sn, Ge, Ti, Fe, Zr, Zn, Ce, Bi, Sr, Mn, Li, Na, K and more preferably Mg, Ca, Al, Ti, Zn, Sn, Ce, Fe.

Suitable solvents are those used in process stage a).

The reaction is preferably carried out in an aqueous medium.

Preference is given to the reaction in a modified solvent system. For this, acidic components, solubilizers, foam inhibitors, etc. are added.

Preferably, the adducts of alkylphosphonous acid derivative (I) and diester-forming olefin (II), their acids, esters and/or alkali metal salts are reacted with metal compounds of Mg, Ca, Al, Zn, Ti, Sn, Zr, Ce or Fe to form the adducts of alkylphosphonous acid and diester-forming olefin (II) of these metals.

The reaction is carried out in a molar ratio of the adducts of alkylphosphonous acid derivative (I) and diester-forming olefin (II) to metal in the range from 8:1 to 1:3 (for tetravalent metal ions or metals having a stable tetravalent oxidation state), from 6:1 to 1:3 (for trivalent metal ions or metals having a stable trivalent oxidation state), from 4:1 to 1:3 (for divalent metal ions or metals having a stable divalent oxidation state) and from 3:1 to 1:4 (for monovalent metal ions or metals having a stable monovalent oxidation state).

Preferably, the esters and/or alkali metal salts of the adducts of alkylphosphonous acid and diester-forming olefin (II) are converted into the corresponding acid and the latter is reacted with metal compounds of Mg, Ca, Al, Zn, Ti, Sn, Zr, Ce or Fe to form the adducts of alkylphosphonous acid and diester-forming olefin of these metals.

Preferably, the acids and esters of the adducts of alkylphosphonous acid and diester-forming olefin (II) are converted into an alkali metal salt and the latter is reacted with metal compounds of Mg, Ca, Al, Zn, Ti, Sn, Zr, Ce or Fe to form the adducts of alkylphosphonous acid and diester-forming olefin (II) of these metals.

The metal compounds of Mg, Ca, Al, Zn, Ti, Sn, Zr, Ce or Fe for process stage e) preferably comprise metals, metal oxides, hydroxides, oxide hydroxides, borates, carbonates, hydroxocarbonates, hydroxocarbonate hydrates, mixed metal hydroxocarbonates, mixed metal hydroxocarbonate hydrates, phosphates, sulfates, sulfate hydrates, hydroxosulfate hydrates, mixed metal hydroxosulfate hydrates, oxysulfates, acetates, nitrates, fluorides, fluoride hydrates, chlorides, chloride hydrates, oxychlorides, bromides, iodides, iodide hydrates, carboxylic acid derivatives and/or alkoxides.

The metal compounds preferably comprise aluminum chloride, aluminum hydroxide, aluminum nitrate, aluminum sulfate, titanyl sulfate, zinc nitrate, zinc oxide, zinc hydroxide and/or zinc sulfate.

Also suitable are aluminum metal, fluoride, hydroxychloride, bromide, iodide, sulfide, selenide; phosphide, hypophosphite, antimonide, nitride; carbide, hexafluorosilicate; hydride, calcium hydride, borohydride; chlorate; sodium aluminum sulfate, aluminum potassium sulfate, aluminum ammonium sulfate, nitrate, metaphosphate, phosphate, silicate, magnesium silicate, carbonate, hydrotalcite, sodium carbonate, borate; thiocyanate; oxide, oxide hydroxide, their corresponding hydrates and/or polyaluminum hydroxy compounds, which preferably have an aluminum content of 9 to 40% by weight.

Also suitable are aluminum salts of mono-, di-, oligo-, polycarboxylic acids such as, for example, aluminum diacetate, acetotartrate, formate, lactate, oxalate, tartrate, oleate, palmitate, stearate, trifluoromethanesulfonate, benzoate, salicylate, 8-oxyquinolate.

Likewise suitable are elemental, metallic zinc and also zinc salts such as for example zinc halides (zinc fluoride, zinc chlorides, zinc bromide, zinc iodide).

Also suitable are zinc borate, carbonate, hydroxide carbonate, silicate, hexafluorosilicate, stannate, hydroxide stannate, magnesium aluminum hydroxide carbonate; nitrate, nitrite, phosphate, pyrophosphate; sulfate, phosphide, selenide, telluride and zinc salts of the oxoacids of the seventh main group (hypohalites, halites, halates, for example zinc iodate, perhalates, for example zinc perchlorate); zinc salts of the pseudohalides (zinc thiocyanate, zinc cyanate, zinc cyanide); zinc oxides, peroxides, hydroxides or mixed zinc oxide hydroxides.

Preference is given to zinc salts of the oxoacids of transition metals (for example zinc chromate(VI) hydroxide, chromite, molybdate, permanganate, molybdate).

Also suitable are zinc salts of mono-, di-, oligo-, polycarboxylic acids, for example zinc formate, acetate, trifluoroacetate, propionate, butyrate, valerate, caprylate, oleate, stearate, oxalate, tartrate, citrate, benzoate, salicylate, lactate, acrylate, maleate, succinate, salts of amino acids (glycine), of acidic hydroxyl functions (zinc phenoxide etc.), zinc p-phenolsulfonate, acetylacetonate, stannate, dimethyldithiocarbamate, trifluoromethanesulfonate.

In the case of titanium compounds, metallic titanium is as is titanium(III) and/or (IV) chloride, nitrate, sulfate, formate, acetate, bromide, fluoride, oxychloride, oxysulfate, oxide, n-propoxide, n-butoxide, isopropoxide, ethoxide, 2-ethylhexyl oxide.

Also suitable is metallic tin and also tin salts (tin(II) and/or (IV) chloride); tin oxides and tin alkoxide such as, for example, tin(IV) tert-butoxide.

Cerium(III) fluoride, chloride and nitrate are also suitable.

In the case of zirconium compounds, metallic zirconium is preferred as are zirconium salts such as zirconium chloride, zirconium sulfate, zirconyl acetate, zirconyl chloride. Zirconium oxides and also zirconium(IV) tert-butoxide are also preferred.

Preferably, the reaction is carried out at a solids content of the salts of adducts of alkylphosphonous acid derivatives and diester-forming olefin in the range from 0.1% to 70% by weight and preferably 5% to 40% by weight.

The reaction is preferably carried out at a temperature of 20 to 250° C., preferably at a temperature of 80 to 120° C.

The reaction carried out at a pressure between 0.01 and 1000 bar, preferably 0.1 to 100 bar.

The reaction preferably takes place during a reaction time in the range from $1*10^{-7}$ to $1*10^2$ h.

Preferably, the adduct of alkylphosphonous acid derivatives and diester-forming olefin of the metals Mg, Ca, Al, Zn, Ti, Sn, Zr, Ce or Fe selectively has a residual moisture content of 0.01% to 10% by weight, preferably of 0.1% to 1% by weight, an average particle size of 0.1 to 2000 μm, preferably of 10 to 500 μm, a bulk density of 80 to 800 g/l, preferably of 200 to 700 g/l, a Pfrengle flowability of 0.5 to 10, preferably of 1 to 5.

Preference is given to the use of the present invention adducts of alkylphosphonous acid derivatives and diester-forming olefins as flame retardants.

The present invention adducts of alkylphosphonous acid derivatives and diester-forming olefins can be incorporated, via their functional groups, as a copolymeric component in thermoplastic polymers such as polyesters for example. In the copolymerization process, the level of adduct is adjusted to achieve the desired level of flame retardancy in the polymer rendered flame-retardant. Compared with conventional flame retardants of the filler or additive type, the advantages are: homogeneous distribution, permanent attachment in the polymer (no bleeding out or offgassing) and improved mechanical toughness and strength properties. Copolymers rendered flame-retardant in this way can also be compounded into polymers. This produces blends which likewise have favorable properties over customary flame retardants of the filler or additive type.

The present invention adducts of alkylphosphonous acid derivatives and diester-forming olefins can, if desired, also be incorporated as described in EP-A-1693403. The flame-retardant thermoplastic molding composition there comprises adducts of alkylphosphonous acid derivatives and diester-forming olefins as a structural unit in the polymer backbone. The adducts of the invention have then been reacted into the polymeric macromolecule through formation of chemical bonds. This can be accomplished through incorporation in the course of the polymerization of the monomers, or through subsequent incorporation by breaking open the macromolecular chain and incorporating the adducts of the invention.

The present invention adducts of alkylphosphonous acid derivatives and diester-forming olefins as a structural unit in the polymer backbone can be randomly distributed on the macromolecule. Accordingly, they may also occasionally occur as end groups (as described in U.S. Pat. No. 3,941,752 for example).

In principle, every possible way of reacting the adducts of the present invention into a polymer can be used. For instance, a thermoplastic polymer can be mixed with adducts of the present invention.

The present invention adducts of alkylphosphonous acid derivatives and diester-forming olefins can also be used as a structural unit in the polymer backbone of polyamides. Typically a polyamide rendered flame-retardant in this way contains between 0.05 and 5.0% by weight of phosphorus and preferably between 0.4 and 2.0% by weight.

Preference is given to using the present invention adducts of alkylphosphonous acid derivatives and diester-forming olefins in the manufacture of flame-retardant thermoplastic polymeric molding compositions.

Preferably, the flame-retardant thermoplastic polymeric molding composition contains 0.5% to 45% by weight of present invention adducts of alkylphosphonous acid derivatives and diester-forming olefins, 0.5% to 95% by weight of thermoplastic polymer or mixtures thereof, the sum total of the components being 100% by weight.

Preferably, the flame-retardant thermoplastic polymeric molding composition contains 0.5% to 40% by weight of present invention adducts of alkylphosphonous acid derivatives and diester-forming olefins, 10% to 85.5% by weight of thermoplastic polymer or mixtures thereof, 2% to 40% by weight of additives, 2% to 40% by weight of filler or reinforcing materials, the sum total of the components being 100% by weight.

Preferably, the additives comprise antioxidants, antistats, blowing agents, further flame retardants, heat stabilizers, impact modifiers, processing aids, lubricants, light stabilizers, antidripping agents, compatibilizers, reinforcing materials, fillers, seed-forming agents, nucleating agents, additives for laser marking, hydrolysis stabilizers, chain extenders, color pigments, softeners, plasticizers and/or plasticizing agents.

Preferred additives are also aluminum trihydrate, antimony oxide, brominated aromatic or cycloaliphatic hydrocarbons, phenols, ethers, chloroparaffin, hexachlorocyclopentadiene adducts, red phosphorus, melamine derivatives, melamine cyanurates, ammonium polyphosphates and magnesium hydroxide. Preferred additives are also further flame retardants, more particularly salts of dialkylphosphinic acids.

The polymer, preferably comprises a thermoplastic or thermoset polymer.

Preferably, the thermoplastic polymers comprise polymers of mono- or diolefins, for example polypropylene, polyisobutylene, poly-1-butene, poly-4-methyl-1-pentene, polyisoprene or polybutadiene and also polymers of cycloolefins, for example of cyclopentene or of norbornene; also polyethylene (which may have crosslinking if desired), e.g., high density polyethylene (HDPE), high density high molecular weight polyethylene (HDPE-HMW), high density ultrahigh molecular weight polyethylene (HDPE-UHMW), medium density polyethylene (MDPE), low density polyethylene (LDPE), linear low density polyethylene (LLDPE), low density branched polyethylene (VLDPE), and also mixtures thereof.

Preferably, the thermoplastic polymers comprise copolymers of mono- and diolefins with one another or with other vinyl monomers, e.g., ethylene-propylene copolymers, linear low density polyethylene (LLDPE) and mixtures thereof with low density polyethylene (LDPE), propylene-1-butene copolymers, propylene-isobutylene copolymers, ethylene-1-butene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and copolymers thereof with carbon monoxide, and ethylene-acrylic acid copolymers and their salts (ionomers), and also terpolymers of ethylene with propylene and a diene, such as hexadiene, dicyclopentadiene or ethylidene-norbornene; further mixtures of such copolymers with one another, e.g., polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers and polyalkylene-carbon monoxide copolymers of alternating or random structure and mixtures of these with other polymers such as polyamides for example.

Preferably, the polymers comprise hydrocarbonaceous resins ($C_5$-$C_9$ for example) including hydrogenated modifications thereof (tackifier resins for example) and mixtures of polyalkylenes and starch.

Preferably, the thermoplastic polymers comprise polystyrene, poly(p-methylstyrene) and/or poly(alpha-methylstyrene).

Preferably, the thermoplastic polymers comprise copolymers of styrene or alpha-methylstyrene with dienes or acrylic derivatives, for example styrene-butadiene, styrene-acrylonitrile, styrene-alkyl methacrylate, styrene-butadiene-alkyl acrylate and styrene-butadiene-alkyl methacrylate, styrene-maleic anhydride, styrene-acrylonitrile-methyl acrylate; mixtures of high impact strength from styrene copolymers and another polymer, for example a polyacrylate, a diene polymer or an ethylene-propylene-diene terpolymer; also block copolymers of styrene, for example styrene-butadiene-styrene, styrene-isoprene-styrene, styrene-ethylene/butylene-styrene or styrene-ethylene/propylene-styrene.

Preferably, the thermoplastic polymers comprise graft copolymers of styrene or alpha-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on poly(alkyl acrylate)s or poly(alkyl methacrylate)s, styrene and acrylonitrile on acrylate-butadiene copolymers, and also their mixtures, as so-called ABS (acrylonitrile-butadiene-styrene), MBS (methyl methacrylate-butadiene-styrene), ASA (acrylonitrile-styrene-acrylate) or AES (acrylonitrile-ethylene-styrene) polymers.

Preferably, the thermoplastic polymers comprise halogen-containing polymers, for example polychloroprene, chlorinated rubber, chlorinated or brominated copolymer formed from isobutylene-isoprene (halogenated butyl rubber), chlorinated or chlorosulfonated polyethylene, copolymers of ethylene and chlorinated ethylene, epichlorohydrin homo- and copolymers, more particularly polymers formed from halogen-containing vinyl compounds, e.g., polyvinyl chloride, polyvinylidene chloride, polyvinyl fluoride, polyvinylidene fluoride; and also copolymers thereof, such as vinyl chloride-vinylidene chloride, vinyl chloride-vinyl acetate or vinylidene chloride-vinyl acetate.

Preferably, the thermoplastic polymers comprise polymers derived from alpha,beta-unsaturated acids and derivatives thereof, such as polyacrylates and polymethacrylates, butyl acrylate-impact modified polymethyl methacrylates, polyacrylamides and polyacrylonitriles and copolymers of the recited monomers with each other or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

Preferably, the thermoplastic polymers comprise polymers derived from unsaturated alcohols and amines or their acetals or acyl derivatives, such as polyvinyl alcohol, polyvinyl acetate, polyvinyl stearate, polyvinyl benzoate, polyvinyl maleate, polyvinyl butyral, polyallyl phthalate, polyallyl melamine; and also their copolymers with olefins.

Preferably, the thermoplastic polymers comprise homo- and copolymers of cyclic ethers, such as polyalkylene glycols, polyethylene oxide, polypropylene oxide or their copolymers with bisglycidyl ethers.

Preferably, the polymers comprise thermoplastic polyacetals, such as polyoxymethylene, and also such polyoxymethylenes as contain comonomers, for example ethylene oxide; polyacetals modified with thermoplastic polyurethanes, acrylates or MBS.

Preferably, the thermoplastic polymers comprise polyphenylene oxides and sulfides and mixtures thereof with styrene polymers or polyamides.

Preferably, the thermoplastic polymers comprise polyurethanes derived from polyethers, polyesters and polybutadienes having terminal hydroxyl groups on the one hand and aliphatic or aromatic polyisocyanates on the other, and also precursors thereof.

Preferably, the thermoplastic polymers comprise polyamides and copolyamides derived from diamines and dicarboxylic acids and/or from amino carboxylic acids or the corresponding lactams, such as nylon-4, nylon-6 (Akulon® K122, DSM; Zytel® 7301, from DuPont; Durethan® B 29, from Bayer), nylon-6,6 (Zytel® 101, from DuPont; Durethan® A30, Durethan® AKV, Durethan® AM, from Bayer; Ultramid® A3, from BASF) -6,10; -6,9; -6,12; -4,6; -12,12; nylon-11, nylon-12 (Grillamid® L20, from Ems Chemie), aromatic polyamides based on m-xylene, diamine and adipic acid; polyamides produced from hexamethylenediamine and iso- and/or terephthalic acid and optionally an elastomer as modifier, e.g., poly-2,4,4-trimethylhexamethyleneterephthalamide or poly-m-phenyleneisophthalamide; block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. Also with EPDM or ABS-modified polyamides or copolyamides; and also polyamides condensed during processing ("RIM polyamide systems").

Preferably, the polymers comprise polyureas, polyimides, polyamide imides, polyether imides, polyester imides, polyhydantoins and polybenzimidazoles.

Preferably, the thermoplastic polymers comprise polyesters derived from dicarboxylic acids and dialcohols or from hydroxy carboxylic acids or the corresponding lactones, such as polyethylene terephthalate, polybutylene terephthalate (Celanex® 2500, Celanex® 2002, from Celanese; Ultradur®, from BASF), poly-1,4-dimethylolcyclohexane terephthalate, polyhydroxybenzoates, and also block polyether esters derived from polyethers having hydroxyl end groups; and also polyesters modified with polycarbonates or MBS.

Preferably, the thermoplastic polymers comprise polycarbonates, polyester carbonates, also polysulfones, polyether sulfones and polyether ketones.

Preferably, the polymers comprise polyblends of the aforementioned polymers, for example PP/EPDM (polypropylene/ethylene-propylene-diene rubber), polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA-6,6 and copolymers, PA/HDPE, PA/PP, PA/PPO, PBT/PC/ABS or PBT/PET/PC, where PP is polypropylene, EPDM is ethylene-propylene-diene rubber, ABS is acrylonitrile-butadiene-styrene, PVC is polyvinyl chloride, EVA is ethylene-vinyl acetate, MBS is methyl methacrylate-butadiene-styrene, PC is polycarbonate, PBTP is polybutylene terephthalate, CPE is chlorinated polyethylene, POM is polyoxymethylene, PPO is polyphenylene oxide, PUR is polyurethane, PC is polycarbonate, HIPS is high impact polystyrene, PA is polyamide, HDPE is high density polyethylene, PBT is polybutylene terephthalate, PET is polyethylene terephthalate.

Preference is given to using the present invention adducts of alkylphosphonous acid derivatives and diester-forming olefins in the manufacture of flame-retardant polymeric moldings, films, threads and fibers.

Preferably, the flame-retardant polymeric moldings, films, threads and fibers contain 0.5% to 45% by weight of present invention adducts of alkylphosphonous acid derivatives and diester-forming olefins, 0.5% to 98% by weight of thermoplastic polymer or mixtures thereof, 0.5% to 55% by weight of additives and 0.5% to 55% by weight of filler or reinforcing materials.

The invention lastly also provides a process for producing flame-retardant polymeric moldings, which comprises flame-retardant polymeric molding compositions of the present invention being processed by injection molding (on an Aarburg Allrounder injection molding machine for example) and pressing, foam injection molding, internal-gas-pressure injection molding, blow molding, film casting, calendering, laminating or coating at elevated temperatures to form the flame-retardant polymeric molding.

Present invention adducts of alkylphosphonous acid derivatives and diester-forming olefins can be incorporated, via the functional group, as a copolymeric component in thermoset polymers such as, for example, unsaturated polyesters or epoxides.

Preferably, the thermoset polymers comprise unsaturated polyester (UP) resins derived from copolyesters of saturated and unsaturated dicarboxylic acids or their anhydrides with polyhydric alcohols, and also vinyl compounds as crosslinking agents. UP resins are cured by free-radical polymerization with initiators (peroxides for example) and accelerants.

Preferred unsaturated dicarboxylic acids and derivatives for producing the polyester resins are maleic anhydride and fumaric acid.

Preferred saturated dicarboxylic acids are phthalic acid, isophthalic acid, terephthalic acid, tetrahydrophthalic acid, adipic acid.

Preferred diols are 1,2-propanediol, ethylene glycol, diethylene glycol and neopentyl glycol, neopentyl glycol, ethoxylated or propoxylated bisphenol A.

Styrene is the preferred vinyl compound for crosslinking.

Preferred curative systems are peroxides and metal coinitiators e.g. hydroperoxides and cobalt octanoate and/or benzoyl peroxide and aromatic amines and/or UV light and photosensitizers, for example benzoin ether.

Preferred hydroperoxides are di-tert-butyl peroxide, tert-butyl peroctoate, tert-butyl perpivalate, tert-butyl per-2-ethylhexanoate, tert-butyl permaleate, tert-butyl perisobutyrate, benzoyl peroxide, diacetyl peroxide, succinyl peroxide, p-chlorobenzoyl peroxide, dicyclohexyl peroxide dicarbonate.

The amounts in which initiators are used are preferably in the range from 0.1% to 20% by weight and more preferably in the range from 0.2% to 15% by weight, reckoned on the mass of all comonomers.

Preferred metal coinitiators are cobalt, manganese, iron, vanadium, nickel or lead compounds. Preference is given to using metal coinitiators in amounts of 0.05% to 1% by weight, reckoned on the mass of all comonomers.

Preferred aromatic amines are dimethylaniline, dimethyl-p-toluene, diethylaniline and phenyldiethanolamines.

A process for producing flame-retardant copolymers comprises at least one ethylenically unsaturated dicarboxylic anhydride derived from at least one $C_4$-$C_8$ dicarboxylic acid, at least one vinylaromatic compound and a polyol being copolymerized and reacted with present invention adducts of alkylphosphonous acid derivatives and diester-forming olefins.

A process for producing flame-resistant thermoset materials comprises a thermoset resin being mixed with a flame-retardancy component comprising present invention adducts of alkylphosphonous acid derivatives and diester-forming olefins and the resulting mixture being cold pressed at pressures of 3 to 10 bar and temperatures of 20 to 60° C. wet.

A further process for producing flame-resistant thermoset materials comprises a thermoset resin being mixed with present invention adducts of alkylphosphonous acid derivatives and diester-forming olefins and the resulting mixture being hot pressed at pressures of 3 to 10 bar and temperatures of 80 to 150° C. wet.

Preferably, the polymers comprise crosslinked epoxy resins derived from aliphatic, cycloaliphatic, heterocyclic or aromatic glycidyl compounds, for example from bisphenol A diglycidyl ethers, bisphenol F diglycidyl ethers, which are crosslinked by means of customary curatives and/or accelerants.

Suitable glycidyl compounds are bisphenol A diglycidyl esters, bisphenol F diglycidyl esters, polyglycidyl esters of phenol-formaldehyde resins and cresol-formaldehyde resins, polyglycidyl esters of phthalic acid, isophthalic acid and terephthalic acid and also of trimellitic acid, N-glycidyl compounds of aromatic amines and heterocyclic nitrogen bases and also di- and polyglycidyl compounds of polyhydric aliphatic alcohols.

Suitable curatives are polyamines such as diethylenetriamine, triethylenetetramine, aminoethylpiperazine, isophoronediamine, polyamidoamine, diaminodiphenylmethane, diaminodiphenol sulfones and dicyandiamide, also polybasic acids or their anhydrides such as, for example, phthalic anhydride, maleic anhydride, tetrahydrophthalic anhydride, methyltetrahydrophthalic anhydride, hexahydrophthalic anhydride and methylhexahydrophthalic anhydride and also phenols such as, for example, phenol novolak resin, cresol-novolak resin, dicyclopentadiene-phenol adduct resin, phenol aralkyl resin, cresol aralkyl resin, naphthol aralkyl resin, biphenol-modified phenol aralkyl resin, phenol-trimethylolmethane resin, tetraphenylolethane resin, naphthol-novolak resin, naphthol-phenol-cocondensate resin, naphthol-cresol-cocondensate resin, biphenol-modified phenolic resin and aminotriazine-modified phenolic resin. All curatives can be used singly or combined with each other.

Suitable catalysts/accelerants for the crosslinking in the polymerization are tertiary amines, benzyldimethylamine, N-alkylpyridines, imidazole, 1-methylimidazole, 2-methylimidazole, 2-ethyl-4-methylimidazole, 2-ethyl-4-methylimidazole, 2-phenylimidazole, 2-heptadecylimidazole, metal salts of organic acids, Lewis acids and amine complex salts.

Epoxy resins are useful for encapsulating electrical/electronic components and for saturating and impregnating operations. In electrical engineering, epoxy resins are overwhelmingly rendered flame-resistant and used for circuit boards and insulators.

Preferably, the polymers comprise crosslinked polymers derived from aldehydes on the one hand and phenols, urea or melamine on the other, such as phenol-formaldehyde, urea-formaldehyde and melamine-formaldehyde resins. Preferably, the polymers comprise crosslinkable acrylic resins derived from substituted acrylic esters, for example from epoxy acrylates, urethane acrylates or polyester acrylates.

Preferably, the polymers comprise alkyd resins, polyester resins and acrylate resins crosslinked with melamine resins, urea resins, isocyanates, isocyanurates, polyisocyanates or epoxy resins.

The invention also provides a flame-retardant polyurethane molding composition produced by reaction of 0.1 to 50 parts by weight of present invention adducts of alkylphosphonous acid derivatives and diester-forming olefins with 30 to 65 parts by weight of polyisocyanate and 30 to 65 parts by weight of polyol.

The process for producing a flame-retardant polyurethane molding composition comprises 170 to 70 parts by weight, preferably 130 to 80 parts by weight of polyisocyanates being made to react with 100 parts by weight of polyol, 0.1 to 50 parts by weight of present invention adducts of alkylphosphonous acid derivatives and diester-forming olefins and 0.1 to 4 parts by weight and more preferably 1 to 2 parts by weight of catalyst and optionally foamed with 0.1 to 1.8 parts by weight and preferably 0.3 to 1.6 parts by weight of blowing agent.

Preferred polyols are alkene oxide adducts of ethylene glycol, 1,2-propanediol, bisphenol A, trimethylolpropane, glycerol, pentaerythritol, sorbitol, sugar, degraded starch, ethylenediamine, diaminotoluene and/or aniline, which serve as an initiator. The preferred oxyalkylating agents preferably contain 2 to 4 carbon atoms, particular preference being given to ethylene oxide and propylene oxide.

Preferred polyester polyols are obtained by polycondensation of a polyalcohol such as ethylene glycol, diethylene glycol, propylene glycol, 1,4-butanediol, 1,5-pentanediol, methylpentanediol, 1,6-hexanediol, trimethylolpropane, glycerol, pentaerythritol, diglycerol, fructose and/or sorbitol with a dibasic acid such as oxalic acid, malonic acid, succinic acid, tartaric acid, adipic acid, sebacic acid, maleic acid, fumaric acid, phthalic acid and/or terephthalic acid. These polyester polyols can be used singly or combined.

Suitable polyisocyanates are aromatic, alicyclic or aliphatic polyisocyanates having no fewer than two isocyanate groups and mixtures thereof. Preference is given to aromatic polyisocyanates such as tolyl diisocyanate, methylenediphenyl diisocyanate, naphthylene diisocyanates, xylylene diisocyanate, tris(4-isocyanatophenyl)methane and polymethylene polyphenylene diisocyanates; alicyclic polyisocyanates such as methylene diphenyl diisocyanate, tolyl diisocyanate; aliphatic polyisocyanates and hexamethylene diisocyanate, isophorone diisocyanate, demeryl diisocyanate, 1,1-methylenebis(4-isocyanatocyclohexane-4,4'-diisocyanatodicyclohexylmethane isomer mixture, 1,4-cyclohexyl diisocyanate, Desmodur® grades (Bayer) and lysine diisocyanate and mixtures thereof.

Suitable polyisocyanates are modified products obtained by reaction of polyisocyanate with polyol, urea, carbodiimide and/or biuret.

Suitable catalysts for preparing polyurethane are strong bases, alkali metal salts of carboxylic acids or aliphatic tertiary amines. Preference is given to quaternary ammonium hydroxide, alkali metal hydroxide or alkoxide, sodium or potassium acetate, potassium octoate, sodium benzoate, 1,4-diazabicyclo[2.2.2]octane, N,N,N',N'-tetramethylhexamethylenediamine, N N,N',N'-tetramethylpropylenediamine, N,N,N',N',N''-pentamethyldiethylenetriamine, N,N'-di($C_1$-$C_2$)-alkylpiperazine, trimethylaminoethylpiperazine, N,N-dimethylcyclo-hexylamine, N,N-dimethylbenzylamine, N-methylmorpholine, N-ethylmorpholine, trimethylamine, triethylamine, tributylamine, triethylenediamine, bis(dimethylamino-alkyl)piperazines, N,N,N',N'-tetramethylethylenediamine, N,N-diethylbenzylamine, bis(N,N-diethylaminoethyl) adipate, N,N,N',N'-tetramethyl-1,3-butanediamine, N,N-diethyl[beta]phenylethylamine, 1,2-dimethylimidazole, 2-methylimidazole etc.

The weight ratio of polyisocyanate to polyol is preferably 170:70 and more preferably 130:80 based on 100 parts by weight of the polyol.

The weight ratio of the catalyst is preferably in the range from 0.1 to 4 parts by weight and more preferably from 1 to 2 parts by weight based on 100 parts by weight of the polyol.

Preferred blowing agents for polyurethanes are water, hydrocarbons, hydrochlorofluorocarbon, hydrofluorocarbon, etc. The amount of blowing agent for polyurethanes is in the range from 0.1 to 1.8 parts by weight, preferably in the range from 0.3 to 1.6 parts by weight and more particularly in the range from 0.8 to 1.6 parts by weight based on 100 parts by weight of the polyol.

The examples which follow illustrate the invention.

Production, processing and testing of flame-retardant polymeric molding compositions and flame-retardant polymeric moldings The flame-retardant components are mixed with the polymeric pellets and any additives and incorporated on a twin-screw extruder (Leistritz LSM® 30/34) at temperatures of 230 to 260° C. (glassfiber-reinforced PBT) or of 260 to 280° C. (glassfiber-reinforced PA 66). The homogenized polymeric strand was hauled off, water bath cooled and then pelletized.

After sufficient drying, the molding compositions were processed on an injection molding machine (Aarburg Allrounder) at melt temperatures of 240 to 270° C. (glassfiber-reinforced PBT) or of 260 to 290° C. (glassfiber-reinforced PA 66) to give test specimens. The test specimens are subsequently flammability tested and classified using the UL 94 (Underwriter Laboratories) test.

UL 94 (Underwriter Laboratories) fire classification was determined on test specimens from each mixture, using test specimens 1.5 mm in thickness.

The UL 94 fire classifications are as follows:
V-0: Afterflame time never longer than 10 sec, total of afterflame times for 10 flame applications not more than 50 sec, no flaming drops, no complete consumption of the specimen, afterglow time for specimens never longer than 30 sec after end of flame application
V-1: Afterflame time never longer than 30 sec after end of flame application, total of afterflame times for 10 flame applications not more than 250 sec, afterglow time for specimens never longer than 60 sec after end of flame application, other criteria as for V-0
V-2: Cotton indicator ignited by flaming drops, other criteria as for V-1
Not classifiable (ncl): does not comply with fire classification V-2.

Some investigated specimens were also tested for their LOI value. The LOI (Limiting Oxygen Index) value is determined according to ISO 4589. According to ISO 4589, the LOI is the lowest oxygen concentration in volume percent which in a mixture of oxygen and nitrogen will support combustion of the plastic. The higher the LOI value, the greater the flammability resistance of the material tested.
LOI 23 flammable
LOI 24-28 potentially flammable
LOI 29-35 flame resistant
LOI >36 particularly flame-resistant

EXAMPLE 1

At room temperature, a three-neck flask equipped with stirrer and high-performance condenser is initially charged with 188 g of water and this initial charge is devolatilized by stirring and passing nitrogen through it. Then, under nitrogen, 0.2 mg of palladium(II) sulfate and 2.3 mg of tris(3-sulfophenyl)phosphine trisodium salt are added, the mixture is stirred, and then 66 g of phosphinic acid in 66 g of water are added. The reaction solution is transferred to a 2 l Büchi reactor and charged with ethylene under superatmospheric pressure while stirring and the reaction mixture is heated to 80° C. After 28 g of ethylene have been taken up, the system is cooled down to room temperature and free ethylene is discharged. The reaction mixture is freed of solvent on a rotary evaporator. The residue is admixed with 100 g of completely ion-free water and at room temperature stirred. The resulting residue is filtered and the filtrate is extracted with toluene, thereafter freed of solvent on a rotary evaporator and the ethylphosphonous acid obtained is collected.

EXAMPLE 2

Example 1 is repeated with 66 g of phosphinic acid, 188 g of butanol, 28 g of ethylene, 0.47 mg of tris(dibenzylideneacetone)dipalladium and 0.63 mg of 4,5-bis(diphenylphosphino)-9,9-dimethylxanthene being reacted, after which the last two are removed and a further 124 g of n-butanol are added. At a reaction temperature of 80-110° C., the water formed is removed by azeotropic distillation. The product (ethylphosphonous acid) is purified by distillation at 1 mbar.

EXAMPLE 3

94.1 g of ethylphosphonous acid (prepared as in Example 1) and 52.0 g of itaconic acid are heated to 160° C. in a four-neck round-bottom flask equipped with stirrer, reflux condenser, thermometer and nitrogen inlet. After the reaction has kicked off, the mixture is stirred for 15 min, at which point a further 36.4 g of itaconic acid are added followed after a further 30 min by a further 41.6 g of itaconic acid. Volatile constituents are distilled off at reduced pressure to obtain 220 g of adduct formed from ethylphosphonous acid and itaconic acid, this adduct containing 13.4% of phosphorus. An adduct of oxa-10-phosphaphenanthrene with itaconic acid contained just 9% of phosphorus.

EXAMPLE 4

94.1 g of ethylphosphonous acid (prepared as in Example 1) and 116 g of maleic acid are introduced into a four-neck round-bottom flask equipped with stirrer, reflux condenser, thermometer and nitrogen inlet. Over 1 h, at about 10° C., 16.4 g of a 5% solution of AIBN in glacial acetic acid are added dropwise. Thereafter, the solvent is distilled off in vacuo to obtain 191 g of adduct formed from ethylphosphonous acid and maleic acid, this adduct containing 14.5% of phosphorus. An adduct of oxa-10-phosphaphenanthrene with maleic acid contained just 9.3% of phosphorus.

EXAMPLE 5

94.1 g of ethylphosphonous acid (prepared as in Example 1) and 144 g of dimethyl fumarate are introduced into a four-neck round-bottom flask equipped with stirrer, reflux condenser, thermometer and nitrogen inlet, heated to 150° C. and then subsequently stirred for 2 h. Volatile constituents are distilled off at reduced pressure to obtain 226 g of adduct formed from ethylphosphonous acid and dimethyl fumarate, which adduct contains 13.1% of phosphorus. An adduct of oxa-10-phosphaphenanthrene with dimethyl fumarate contained just 8.6% of phosphorus.

EXAMPLE 6

150 g of n-butyl ethylphosphonite (prepared as in Example 2) and 116 g of fumaric acid are initially charged in 217.4 g of butanol and heated to the boil. While stirring, 13.0 g of Wako V65B initiator dissolved in 130.4 g of butanol are metered in. The solvent is distilled off in vacuo to obtain 240 g of adduct formed from n-butyl ethylphosphonite and fumaric acid, which adduct contains 11.6% of phosphorus.

EXAMPLE 7

158 g of dimethyl itaconate are heated to 150° C. under nitrogen and 150 g of n-butyl ethylphosphonite (prepared as in Example 2) are added by metered addition with stirring. Volatile constituents are distilled off at reduced pressure to obtain 296 g of adduct formed from n-butyl ethylphosphonite and dimethyl itaconate, which adduct contains 10.4% of phosphorus.

EXAMPLE 8

150 g of n-butyl ethylphosphonite (prepared as in Example 2) and 242 g of dibutyl itaconate in 217.4 g of butanol are heated to the boil. While stirring, 13 g of Wako V65B initiator dissolved in 130 g of butanol are metered in. The solvent is distilled off in vacuo to obtain 377 g of adduct formed from n-butyl ethylphosphonite and dibutyl itaconate, which adduct contains 7.7% of phosphorus.

EXAMPLE 9

A five-neck flask equipped with thermometer, reflux condenser, stirrer and dropping funnel is initially charged with 228 g of dibutyl maleate and 150 g of n-butyl ethylphosphonite. While stirring, 5 g of sodium butoxide (30%) are added dropwise at such a rate that the temperature does not rise above 60° C. and then volatile constituents are distilled off in vacuo to obtain 363 g of adduct formed from n-butyl ethylphosphonite and dibutyl maleate, which adduct contains 8.1% of phosphorus.

EXAMPLE 10

94.1 g of ethylphosphonous acid (prepared as in Example 1) and 98.1 g of maleic anhydride are reacted by heating in a reaction vessel to 150° C. under nitrogen, obtaining 183 g of adduct formed from ethylphosphonous acid and maleic anhydride.

EXAMPLE 11

150 g of n-butyl ethylphosphonite (prepared as in Example 2) and 112 g of itaconic anhydride are reacted by heating to 150° C. in a reaction vessel under nitrogen, obtaining 257 g of adduct formed from n-butyl ethylphosphonite and itaconic anhydride, which adduct contains 11.5% of phosphorus.

EXAMPLE 12

150 g of n-butyl ethylphosphonite (prepared as in Example 2) and 108 g of benzoquinone are added to 400 g of 2-ethoxyethanol and while stirring heated to 70° C., subsequently stirred and then cooled down. The product is filtered off, washed with 72 ml of 2-ethoxyethanol and 72 ml of methanol and dried at 130° C. in vacuo to obtain 220 g of adduct formed from n-butyl ethylphosphonite and benzoquinone, which adduct contains 11.9% of phosphorus.

EXAMPLE 13

In a high pressure stirred vessel, 94.1 g of ethylphosphonous acid (prepared as in Example 1) and 112 g of itaconic anhydride are reacted by heating at 150° C. under nitrogen.

After cooling, 155 g of ethylene glycol and 0.4 g of potassium titanyl oxalate are added and the mixture is stirred some more. Volatiles are distilled off by evacuating to leave 314 g of ethylene glycol ester of the adduct formed from ethylphosphonous acid and itaconic acid, the ester containing 10% of phosphorus.

EXAMPLE 14

94.1 g of ethylphosphonous acid (prepared as in Example 1) and 116 g of maleic acid are introduced into a four-neck round-bottom flask equipped with stirrer, condenser, thermometer and nitrogen inlet. Over 1 h, at about 90° C., 16.4 g of a 5% solution of AIBN in ethylene glycol are added dropwise. Then, 330 g of ethylene glycol are added, followed by heating to 200° C. Water is distilled off in a mixture with ethylene glycol over 4 h to leave 248 g of ethylene glycol ester of the adduct of ethylphosphonous acid and maleic acid, the ester containing 12.5% of phosphorus.

EXAMPLE 15

9.4 g of ethylphosphonous acid (prepared as in Example 1) and 13 g of itaconic acid are introduced into a four-neck round-bottom flask equipped with stirrer, condenser, thermometer and nitrogen inlet. The reaction solution is heated to 160° C. for 1 h. Volatile constituents are distilled off at reduced pressure to obtain 22 g of adduct formed from ethylphosphonous acid and itaconic acid. Then, 290 g of terephthalic acid, 188 g of ethylene glycol, 0.29 g of calcium acetate are added followed by heating to 200° C. for 2 h. Thereafter, 0.29 g of trisodium phosphate anhydrate and 0.14 g of antimony(III) oxide are added, followed by heating to 280° C. and gradual evacuating over one hour. The polymeric product (420 g) contains 0.7% of phosphorus, the intrinsic viscosity is 0.67, the LOI is 33.4.

EXAMPLE 16

94.1 g of ethylphosphonous acid (prepared as in Example 1) and 13 g of itaconic acid are introduced into a four-neck round-bottom flask equipped with stirrer, condenser, thermometer and nitrogen inlet. The reaction solution is heated to 160° C. and volatile constituents are distilled off at reduced pressure to leave 220 g of adduct formed from ethylphosphonous acid and itaconic acid, which is transferred into a three-neck flask. 124 g of ethylene glycol are added and, at 160° C., the water formed in the course of the esterification is stripped off. One tenth of the reaction product thus obtained is admixed with 290 g of terephthalic acid, 176 g of ethylene glycol, 0.29 g of calcium acetate and heated to 200° C. for 2 h. Then, 0.29 g of trisodium phosphate anhydrate and 0.14 g of antimony(III) oxide are added, followed by heating to 280° C. and gradual evacuating over one hour. The polymeric product (about 420 g) contains 0.7% of phosphorus, the intrinsic viscosity is 0.68, the LOI is 32.1, that of untreated polyethylene terephthalate is about 25.

EXAMPLE 17

9.41 g of ethylphosphonous acid (prepared as in Example 1) and 11.6 g of maleic acid are introduced into a four-neck round-bottom flask equipped with stirrer, condenser, thermometer and nitrogen inlet. The reaction solution is heated to 160° C. for 1 h and volatile constituents are distilled off at reduced pressure to leave about 19 g of adduct formed from ethylphosphonous acid and maleic acid. Then, 367 g of dimethyl terephthalate, 238 g of 1,4-butanediol, 0.22 g of tetrabutyl titanate and 0.05 g of lithium acetate are added and the mixture is initially heated for 2 h with stirring at 130 to 180° C. and then at 270° C. at reduced pressure. The polymeric product (503 g) contains 0.6% of phosphorus, the intrinsic viscosity is 0.96, the LOI is 35, that of untreated polybutylene terephthalate is 23.

EXAMPLE 18

9.41 g of ethylphosphonous acid (prepared as in Example 1) and 11.6 g of maleic acid are introduced into a four-neck round-bottom flask equipped with stirrer, condenser, thermometer and nitrogen inlet. The reaction solution is heated to 160° C. Volatile constituents are distilled off at reduced pressure to leave 19 g of adduct formed from ethylphosphonous acid and maleic acid, which is transferred to a three-neck flask. 15.2 g of 1,3-propylene glycol are added and at 160° C. the water formed in the course of the esterification is stripped off. Then, 367 g of dimethyl terephthalate, 186 g of 1,3-propanediol, 0.22 g of tetrabutyl titanate and 0.05 g of lithium acetate are added and the mixture is initially heated for 2 h with stirring at 130 to 180° C. and then at 270° C. at reduced pressure. The polymeric product (480 g) contains 0.6% of phosphorus, the intrinsic viscosity is 0.94, the LOI is 37.

EXAMPLE 19

A five-neck flask equipped with thermometer, reflux condenser, stirrer and dropping funnel is initially charged with 228 g of dibutyl maleate and 150 g of n-butyl ethylphosphonite (prepared as in Example 2). While stirring, 5 g of sodium butoxide (30%) are added dropwise at such a rate that the temperature does not rise above 60° C. The mixture is allowed to react for a further 30 min and volatile constituents are distilled off in vacuo. Then, some drops of concentrated hydrochloric acid and 235 g of water are added, followed by refluxing. While adding a further 60 g of water, butanol is gradually distilled off to obtain 195 g of the adduct of ethylphosphonous acid and maleic acid.

EXAMPLE 20

Preparation of an Epoxy Resin

In a 250 ml five-neck flask equipped with reflux condenser, stirrer, thermometer and nitrogen inlet 100 g of a bisphenol A bisglycidyl ether having an epoxy value of 0.55 mol/100 g (Beckopox EP 140, from Solutia) and 30 g (0.134 mol) of an adduct formed from ethylphosphonous acid and itaconic acid (prepared as in Example 3) are heated to not more than 150° C. with stirring. A clear melt forms after 30 min. After a further hour of stirring at 150° C. the melt is cooled down and comminuted with a mortar and pestle to obtain 124.8 g of a flame-retardant epoxy resin in the form of a white powder having a phosphorus content of 3.2% by weight.

EXAMPLE 21

Preparation of a UP Resin

In a 2 l flask equipped with stirrer, water trap, thermometer, reflux condenser and nitrogen inlet 29.36 g of phthalic anhydride, 19.6 g of maleic anhydride, 15.2 g of propylene glycol, 25.3 g of di-2-hydroxyethyl ester of the adduct formed from ethylphosphonous acid and itaconic acid (prepared as in Example 3), 20 g of xylene and 50 mg of hydroquinone are heated to 100° C. with stirring and nitrogen being passed therethrough. As soon as the exothermic reaction ensues the heating is removed. After the reaction has died down stirring is continued at about 190° C. After 14 g of water have been separated off, the xylene is distilled off to obtain 88 g of a flame-retardant UP resin.

Chemicals used:

| ITA | itaconic acid | MDB | dibutyl maleate |
| MLA | maleic acid | MAH | maleic anhydride |
| FDM | dimethyl fumarate | IAH | itaconic anhydride |
| FMA | fumaric acid | BCH | benzoquinone |
| IDM | dimethyl itaconate | EG | ethylene glycol |
| IDB | dibutyl itaconate | EPOS | ethylphosphonous acid |

TABLE

| Ex. | | [g] | DBO | [g] | Ester former | [g] | Adduct | Yield [g] | P content [%] |
|---|---|---|---|---|---|---|---|---|---|
| 3 | ethylphosphonous acid | 94.1 | itaconic acid | 130 | — | — | ethylphosphonous acid-itaconic acid | 220 | 13.4 |
| 4 | ethylphosphonous acid | 94.1 | maleic acid | 116 | — | — | ethylphosphonous acid-maleic acid | 191 | 14.5 |
| 5 | ethylphosphonous acid | 94.1 | dimethyl fumarate | 144 | — | — | ethylphosphonous acid-FMDE | 226 | 13.1 |
| 6 | n-butyl ethylphosphonite | 150 | fumaric acid | 116 | — | — | ethylphosphonous acid-n-Bu-fumaric acid | 240 | 11.6 |
| 7 | n-butyl ethylphosphonite | 150 | dimethyl itaconate | 158 | — | — | ethylphosphonous acid-dimethyl n-Bu-itaconate | 296 | 10.4 |
| 8 | n-butyl ethylphosphonite | 150 | dibutyl itaconate | 242 | — | — | ethylphosphonous acid-dibutyl n-Bu-itaconate | 377 | 7.7 |
| 9 | n-butyl ethylphosphonite | 150 | dibutyl maleate | 228 | — | — | ethylphosphonous acid-dibutyl n-Bu-maleate | 363 | 8.1 |
| 10 | ethylphosphonous acid | 94.1 | maleic anhydride | 98.1 | — | — | ethylphosphonous acid-maleic acid | 183 | 16.5 |
| 11 | n-butyl ethylphosphonite | 150 | itaconic anhydride | 112 | — | — | ethylphosphonous acid-n-Bu-itaconic anhydride | 257 | 11.5 |
| 12 | n-butyl ethylphosphonite | 150 | benzoquinone | 108 | — | — | ethylphosphonous acid-n Bu-benzoquinone | 220 | 11.9 |
| 13 | ethylphosphonous acid | 94.1 | itaconic anhydride | 112 | ethylene glycol | 155 | ethylphosphonous acid-IAH-ethylene glycol ester | 314 | 10.0 |
| 14 | ethylphosphonous acid- | 94.1 | maleic acid | 116 | ethylene glycol | 346 | ethylphosphonous acid-maleic acid-ethylene glycol ester | 248 | 12.5 |
| 15 | ethylphosphonous acid | 9.41 | itaconic acid | 13 | ethylene glycol | 188 | not applicable | 420 | 0.7 |
| 16 | ethylphosphonous acid | 94.1 | itaconic acid | 130 | ethylene glycol | 300 | not applicable | 420 | 0.7 |
| 17 | ethylphosphonous acid | 9.41 | maleic acid | 11.6 | BG | 238 | not applicable | 503 | 0.6 |
| 18 | ethylphosphonous acid | 9.41 | itaconic acid | 13 | PG | 201 | not applicable | 480 | 0.6 |
| 19 | n-butyl ethylphosphonite | 150 | dibutyl maleate | 228 | — | — | ethylphosphonous acid-maleic acid | 195 | 14.7 |

What is claimed is:

1. An adduct formed from
a) an alkylphosphonous acid derivative of formula (I)

$$A\text{-}P(=O)(OX)\text{-}H \quad (I)$$

wherein

A is an ethyl, n-propyl, i-propyl, n-butyl, i-butyl, n-pentyl, i-pentyl, n-hexyl, i-hexyl, 2-phenylethyl, 1-phenylethyl, 3-phenylpropyl, 2-phenylpropyl, 2-hydroxyethyl, 3-hydroxypropyl, 2-carboxyethyl, 3-carboxypropyl, 2-acetatoethyl, 3-acetatopropyl, 2-butyratoethyl, 3-butyratopropyl, 2-ethyloxyethyl, 3-ethyloxypropyl, 2-propyloxyethyl, 3-propyloxypropyl, 2-butyloxyethyl, 3-butyloxypropyl, 3-carboxypropyl, 2-aminoethyl, 3-aminopropyl group or a combination thereof, and X is H, $C_1$-$C_{18}$-alkyl, $C_6$-$C_{18}$-aryl, $C_6$-$C_{18}$-arylalkyl, $C_6$-$C_{18}$-alkylaryl, $C_2$-$C_{18}$-alkylene, Mg, Ca, Al, Sb, Sn, Ge, Ti, Fe, Zr, Zn, Ce, Bi, Sr, Mn, Cu, Ni Li, Na, K, H a protonated nitrogen base or a combination thereof, wherein the $C_1$-$C_{18}$-alkyl, $C_6$-$C_{18}$-aryl, $C_6$-$C_{18}$ arylalkyl, $C_6$-$C_{18}$-alkylaryl or $C_2$-$C_{18}$-alkylene is optionally substituted, and b) a diester-forming olefin of formula (II)

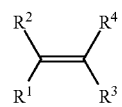

(II)

wherein $R^2$, $R^4$ are the same or different and are $CO_2H$, $CO_2R^5$, $R^6\text{—}CO_2H$ or $R^6\text{—}CO_2R^5$ and $R^1$, $R^3$ are the same or different and are H or $R^5$; or
$R^1$, $R^4$ are the same or different and are $CO_2H$, $CO_2R^5$, $R^6\text{—}CO_2H$ or $R^6\text{—}CO_2R^5$ and
$R^2$, $R^3$ are the same or different and are H or $R^5$; or
$R^2$, $R^4$ are the same or different and are —CO—O—CO—, —CO—S—CO—, —CO—$NR^1$—CO—, or —CO—$PR^1$—CO— and $R^1$, $R^3$ are the same or different and are H or $R^5$; or
$R^1$, $R^2$ are the same or different and are $CO_2H$, CN, $CO_2R^5$, $R^6\text{—}CO_2H$ or $R^6\text{—}CO_2R^5$ and
$R^3$, $R^4$ are the same or different and are H or $R^5$; or
$R^1$, $R^2$ are the same or different and are —$CR_2^3$—CO—O—CO—, —$CR_2^3$—CO—$NR^1$—CO—, —$CR_2^3$—CO—O—CO—$CR_2^3$ or —$CR_2^3$—CO—$NR^1$—CO—$CR_2^3$ and $R^3$, $R^4$ are the same or different and are H or $R^5$; or $R^2$ and $R^4$ each represent —CO—CR$^5$=CR$^5$—CO— and $R^1$, $R^3$ are the same or different and are H are $R^5$;

$R^5$ is $C_1$-$C_{18}$-alkyl, $C_6$-$C_{18}$-aryl, $C_6$-$C_{18}$-arylalkyl or $C_6$-$C_{18}$-alkylaryl;

$R^6$ is $C_2$-$C_{18}$-alkylene, $C_6$-$C_{18}$-arylene, $C_6$-$C_{18}$-alkarylene, $C_6$-$C_{18}$-aralkylene or a combination thereof.

2. The adduct according to claim 1 wherein X is hydrogen, a methyl, ethyl, propyl, butyl, amyl, octyl, ethylhexyl, ethylene glycol, propylene glycol, butylene glycol, benzyl, phenyl, vinyl group, allyl group, lithium, sodium, potassium, magnesium, calcium, barium, aluminum, lead, titanium, iron, zinc, ammonium, anilinium, trimethylammonium, triethylammonium, tripropylammonium, tributylammonium, tetramethylammonium, tetraethylammonium, tetrapropylammonium, tetrabutylammonium, trimethylsilylammonium or N-ethylpiperidine.

3. The adduct according to claim 1, wherein the diester-forming olefin is maleic acid, fumaric acid, itaconic acid, phenylmethylenemalonic acid, their dimethyl, diethyl, dipropyl, diisopropyl and dibutyl esters, maleic anhydride, itaconic anhydride, benzoquinone, naphthoquinone or anthraquinone.

4. A halogen-free process for preparing an adduct of the alkylphosphonous acid derivative (I) and diester forming olefin (II) wherein the adduct is formed from a) an alkylphosphonous acid derivative of formula (I)

A-P(=O)(OX)—H    (I)

wherein

A is an optionally substituted $C_2$-$C_{18}$-alkyl, $C_2C_{18}$-alkylene, $C_6$-$C_{18}$-arylalkyl, $C_6$-$C_{18}$-arylalkyl or a combination thereof, and X is H, $C_1$-$C_{18}$-alkyl, $C_6$-$C_{18}$-aryl, $C_6$-$C_{18}$-arylalkyl, $C_6$-$C_{18}$-alkylaryl, $C_2$-$C_{18}$-alkylene, Mg, Ca, Al, Sb, Sn, Ge, Ti, Fe, Zr, Zn, Ce, Bi, Sr, Mn, Cu, Ni, Li, Na, K, H a protonated nitrogen base or a combination thereof, wherein the $C_1$-$C_{18}$-alkyl, $C_6$-$C_{18}$-aryl, $C_6$-$C_{18}$-arylalkyl, $C_6$-$C_{18}$-alkylaryl or $C_2$-$C_{18}$-alkylene is optionally substituted, and b) a diester-forming olefin of formula (II)

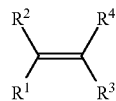

(II)

wherein $R^2$, $R^4$ are the same or different and are CO$_2$H, CO$_2$R$^5$, R$^6$-CO$_2$H or R$^6$-CO$_2$R$^5$ and $R^1$, $R^3$ are the same or different and are H or $R^5$; or $R^1$, $R^4$ are the same or different and are CO$_2$H, CO$_2$R$^5$, R$^6$-CO$_2$H or R$^6$-CO$_2$R$^5$ and $R^2$, $R^3$ are the same or different and are H or $R^5$; or $R^2$, $R^4$ are the same or different and are —CO-O-CO-, —CO-S-CO-, —CO-NR$^1$-CO-, or —CO-PR$^1$-CO- and $R^1$, $R^3$ are the same or different and are H or $R^5$; or $R^1$, $R^2$ are the same or different and are CO$_2$H, CN, CO$_2$R$^5$, R$^6$-CO$_2$H or R$^6$-CO$_2$R$^5$ and $R^3$, $R^4$ are the same or different and are H or $R^5$; or $R^1$, $R^2$ are the same or different and are —CR$_2^3$-CO-O-CO-, —CR$_2^3$-CO-NR$^1$-CO-, —CR$_2^3$-CO-O-CO-CR$_2^3$ or —CR$_2^3$-CO-NR$^1$-CO-CR$_2^3$ and $R^3$, $R^4$ are the same or different and are H or $R^5$; or $R^2$ and $R^4$ each represent —CO-CR$^5$=CR$^5$-CO- and $R^1$, $R^3$ are the same or different and are H are $R^5$;

$R^5$ is $C_1$-$C_{18}$-alkyl, $C_6$-$C_{18}$-aryl, $C_6$-$C_{18}$-arylalkyl or $C_6$-$C_{18}$-alkylaryl;

$R^6$ is $C_2$-$C_{18}$-alkylene, $C_6$-$C_{18}$-arylene, $C_6$-$C_{18}$-alkarylene, $C_6$-$C_{18}$-aralkylene or a combination thereof, comprising the steps of a) reacting at least one phosphinic acid source with at least one non-diester-forming olefin (III) in the presence of at least one catalyst A to form an alkylphosphonous acid derivative (I), b) reacting the resulting alkylphosphonous acid derivative (I) with a diester-forming olefin (II) in the presence of at least one catalyst B to form the adduct, wherein the alkylphosphonous acid derivative is of the formula (I)

A-P(=O)(OX)—H    (I)

wherein

A is an optionally substituted $C_2$-$C_{18}$-alkyl, $C_2$-$C_{18}$-alkylene, $C_6$-$C_{18}$-arylalkyl, $C_6$-$C_{18}$-arylalkyl or a combination thereof, and X is H, $C_1$-$C_{18}$-alkyl, $C_6$-$C_{18}$-aryl, $C_6$-$C_{18}$-arylalkyl, $C_6$-$C_{18}$-alkylaryl or $C_2$-$C_{18}$-alkylene, wherein the $C_1$-$C_{18}$-alkyl, $C_6$-$C_{18}$-aryl, $C_6$-$C_{18}$-alkylaryl, $C_6$-$C_{18}$-alkylaryl or $C_2$-$C_{18}$-alkylene is optionally substituted, wherein the at least one catalyst A is selected from the group consisting of transition metals a transition metal compounds, catalyst systems composed of a transition metal a transition metal compound and at least one ligand and a combination thereof, and the at least one catalyst B is selected from the group consisting of peroxide-forming compounds, peroxo compounds, azo compounds, alkali metals, alkaline earth metals, alkali metal hydrides, alkaline earth metal hydrides, alkoxides and combinations thereof.

5. The process according to claim 4 wherein A is an ethyl, n-propyl, i-propyl, n-butyl, i-butyl, n-pentyl, i-pentyl, n-hexyl, i-hexyl, 2-phenylethyl, 1-phenylethyl, 3-phenylpropyl, 2-phenylpropyl, 2-hydroxyethyl, 3-hydroxypropyl, 2-carboxyethyl, 3-carboxypropyl, 2-acetatoethyl, 3-acetatopropyl, 2-butyratoethyl, 3-butyratopropyl, 2-ethyloxyethyl, 3-ethyloxypropyl, 2-propyloxyethyl, 3-propyloxypropyl, 2-butyloxyethyl, 3-butyloxypropyl, 3-carboxypropyl, 2-aminoethyl, 3-aminopropyl group or a combination thereof.

6. The process according to claim 4 wherein X is hydrogen, a methyl, ethyl, propyl, butyl, amyl, octyl, ethylhexyl, ethylene glycol, propylene glycol, butylene glycol, benzyl, phenyl, vinyl group allyl group, lithium, sodium, potassium, magnesium, calcium, barium, aluminum, lead, titanium, iron, zinc, ammonium, anilinium, trimethylammonium, triethylammonium, tripropylammonium, tributylammonium, tetramethylammonium, tetraethylammonium, tetrapropylammonium, tetrabutylammonium, trimethylsilylammonium or N-ethylpiperidine.

7. The process according to claim 4, wherein the diester-forming olefin is of the formula (II)

(II)

wherein $R^2$, $R^4$ are the same or different and are CO$_2$H, CO$_2$R$^5$, R$^6$—CO$_2$H or R$^6$—CO$_2$R$^5$ and $R^1$, $R^3$ are the same or different and are H or $R^5$; or $R^1$, $R^4$ are the same or different and are $CO_2H$, $CO_2R^5$, $R^6$—$CO_2H$ or $R^6$—$CO_2R^5$ and $R^2$, $R^3$ are the same or different and are H or $R^5$; or $R^2$, $R^4$ are the same or different and are —CO—O—CO—, —CO—S—CO—, —CO—NR$^1$—CO—, —CO—PR$^1$—CO— and $R^1$, $R^3$ are the same or different and represent H or $R^5$; or $R^1$, $R^2$ are the same or different and are $CO_2H$, CN, $CO_2R^5$, $R^6$—$CO_2H$ or $R^6$—$CO_2R^5$ and $R^3$, $R^4$ are the same or different and are H or $R^5$; or $R^1$, $R^2$ are the same or different and are —$CR_2^3$—CO—O—CO—, —$CR_2^3$—CO—NR$^1$—CO—, —$CR_2^3$—CO—O—CO—$CR_2^3$ or —$CR_2^3$—CO—NR$^1$—CO—$CR_2^3$ and $R^3$, $R^4$ are the same or different and are H or $R^5$; or $R^2$ and $R^4$ each represent —CO—$CR^5$=$CR^5$—CO— and $R^1$, $R^3$ are the same or different and are H or $R^5$;

$R^5$ is $C_1$-$C_{18}$-alkyl, $C_6$-$C_{18}$-aryl, $C_6$-$C_{18}$-arylalkyl or $C_6$-$C_{18}$-alkylaryl;

$R^6$ is $C_2$-$C_{18}$-alkylene, $C_5$-$C_{18}$-arylene, $C_6$-$C_{18}$-alkarylene or $C_6$-$C_{18}$-aralkylene.

8. The process according to claim 4, wherein the diester-forming olefin is maleic acid, fumaric acid, itaconic acid, phenylmethylenemalonic acid, their dimethyl, diethyl, dipropyl, diisopropyl and dibutyl esters, benzoquinone, naphthoquinone or anthraquinone.

9. The process according to claim 4, wherein the at least one phosphinic acid source is phosphinic acid, a salt of phosphinic acid, an ester of phosphinic acid or mixtures thereof.

10. The process according to claim 4, wherein the non-diester-forming olefin is of the formula (III)

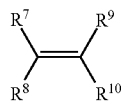

(III)

where $R^7$ to $R^{10}$ are the same or different and are $C_1$-$C_{18}$-alkyl, $C_6$-$C_{18}$-aryl or $C_2$-$C_{18}$-alkylene.

11. The process according to claim 4, wherein the at least one non-diester-forming olefin (III) is ethylene, 1-propylene, 1-butene, 1-pentene, 1-hexene, 1,3-butadiene or a combination thereof.

12. The process according to claim 4, wherein the transition metals, transition metal compounds or both are from the seventh or eighth transition groups.

13. The process according to claim 4, wherein the transition metals, transition metal compounds or both are rhodium, nickel, palladium, ruthenium, platinum or a combination thereof.

14. The process according to claim 4, wherein the at least one catalyst B is hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-t-butyl peroxide, peroxodisulfuric acid, azobisisobutyronitrile, 2,2'-azobis(2-amidinopropane) dihydrochloride, 2,2'-azobis(N,N'-dimethyleneisobutyramidine) dihydrochloride, lithium, lithium hydride, lithium aluminohydride, methyllithium, butyllithium, t-butyllithium, lithium diisopropylamide, sodium, sodium hydride, sodium borohydride, sodium methoxide, sodium ethoxide, sodium butoxide, potassium methoxide, potassium ethoxide, potassium butoxide or a combination thereof.

15. The process according to claim 4, wherein the reaction product obtained from the alkylphosphonous acid derivative (I) and diester-forming olefin (II) after step b) is reacted with an ester former in a step c).

16. The process according to claim 15 wherein the ester formers are selected from the group consisting of $C_1$-$C_{20}$ saturated and unsaturated mono-, di-, tri- or tetrahydric alcohols.

17. The process according to claim 15, wherein the ester formers are methanol, ethanol, propanol, butanol, amyl alcohol, octanol, ethylene glycol, polyethylene glycol, 1,2-propanediol, 1,3-propanediol, butanediol, glycerol, erythritol, pentaerythritol, allyl alcohol, 3-buten-1-ol, 3-hydroxy-1-butene, 3-buten-2-ol, methylvinylcarbinol, 2-methyl-2-propen-1-ol, methallyl alcohol, 2-buten-1-ol, crotyl alcohol, 1-penten-3-ol, trans-2-penten-1-ol, cis-2-penten-1-ol, 3-penten-2-ol, 4-penten-1-ol, 4-penten-2-ol, 1-hexen-3-ol, cis-2-hexen-1-ol, trans-2-hexen-1-ol, cis-3-hexen-1-ol, trans-3-hexen-1-ol, 4-hexen-1-ol, 5-hexen-1-ol, 5-hexen-2-ol, 1-hepten-3-ol, 1-octen-3-ol, trans-2-octen-1-ol, oleyl alcohol, terpene alcohol, propargyl alcohol, 2-butyne-1,4-diol or a combination thereof.

18. The process according to claim 4, wherein the reaction product obtained from the alkylphosphonous acid derivative (I) and diester-forming olefin (II) after step b) is reacted with at least one catalyst C, and saponifying the reaction product.

19. The process according to claim 18, wherein the at least one catalyst C is selected from the group consisting of Brönsted acids, Brönsted bases, water, mineral acids, sulfonic acids, alkali metal hydroxides, alkaline earth metal hydroxides or a combination thereof.

20. A composition comprising an adduct formed from
a) an alkylphosphonous acid derivative of formula (I)

$$A\text{-}P(=O)(OX)\text{—}H \qquad (I)$$

wherein

A is an ethyl, n-propyl, i-propyl, n-butyl, i-butyl, n-pentyl, i-pentyl, n-hexyl, i-hexyl, 2-phenylethyl, 1-phenylethyl, 3-phenylpropyl, 2-phenylpropyl, 2-hydroxyethyl, 3-hydroxpropyl, 2-carboxyethyl, 3-carboxypropyl, 2-acetatoethyl, 3-acetatopropyl, 2-butyratoethyl, 3-butyratopropyl, 2-ethyloxyethyl, 3-ethyloxypropyl, 2-propyloxyethyl, 3-propyloxypropyl, 2-butyloxyethyl, 3-butyloxypropyl, 3-carboxypropyl, 2-aminoethyl, 3-aminopropyl group or a combination thereof, and X is H, $C_1$-$C_{18}$-alkyl, $C_6$-$C_{18}$-aryl, $C_6$-$C_{18}$-arylalkyl, $C_6$-$C_{18}$-alkylaryl, $C_2$-$C_{18}$-alkylene, Mg, Ca, Al, Sb, Sn, Ge, Ti, Fe, Zr, Zn, Ce, Bi, Sr, Mn, Cu, Ni, Li, Na, K, H a protonated nitrogen base or a combination thereof, wherein the $C_1$-$C_{18}$-alkyl, $C_6$-$C_{18}$-aryl, $C_6$-$C_{18}$-arylalkyl, $C_6$-$C_{18}$-alkylaryl or $C_2$-$C_{18}$-alkylene is optionally substituted, and b) a diester-forming olefin of formula (II)

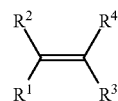

(II)

wherein $R^2$, $R^4$ are the same or different and are $CO_2H$, $CO_2R^5$, $R^6$-$CO_2H$ or $R^6$-$CO_2R^5$ and $R^1$, $R^3$ are the same or different and are H or $R^5$; or $R^1$, $R^4$ are the same or different and are $CO_2H$, $CO_2R^5$, $R^6$-$CO_2H$ or $R^6$-$CO_2R^5$ and $R^2$, $R^3$ are the same or different and are H or $R^5$; or $R^2$, $R^4$ are the same or different and are —CO-O-CO-, —CO-S-CO-, —CO-$NR^1$-CO-, or —CO-$PR^1$-CO- and $R^1$, $R^3$ are the same or different and are H or $R^5$; or $R^1$, $R^2$ are the same or different and are $CO_2H$, CN, $CO_2R^5$, $R^6$-$CO_2H$ or $R^6$-$CO_2R^5$ and $R^3$, $R^4$ are the same or different and are H or $R^5$; or $R^1$, $R^2$ are the same or different and are —$CR_2^3$-CO-O-CO-, —$CR_2^3$-CO-$NR^1$-CO-, —$CR_2^3$-CO-O-CO-$CR_2^3$ or —$CR_2^3$-CO-$NR^1$-CO-$CR_2^3$ and $R^3$, $R^4$ are the same or different and are H or $R^5$; or $R^2$ and $R^4$ each represent —CO-$CR^5$=$CR^5$-CO- and $R^1$, $R^3$ are the same or different and are H are $R^5$;

$R^5$ is $C_1$-$C_{18}$-alkyl, $C_6$-$C_{18}$-aryl, $C_6$-$C_{18}$arylalkyl or $C_6$-$C_{18}$-alkylaryl;

$R^6$ is $C_2$-$C_{18}$alkylene, $C_6$-$C_{18}$-arylene, $C_6$-$C_{18}$-alkarylene, $C_6$-$C_{18}$-aralkylene or a combination thereof, wherein the composition is in the form of an intermediate for further syntheses, a binder, a crosslinker to cure epoxy resins, polyurethanes or unsaturated polyester resins, an accelerant to cure epoxy resins, polyurethanes or unsaturated polyester resins, a polymer stabilizer, a crop protection agent, a therapeutic or additive in therapeutics for humans and animals, a sequestrant, a mineral oil additive, a corrosion control agent, a washing application, a cleaning application or an electronic application.

21. A composition comprising an adduct formed from a) an alkylphosphonous acid derivative of formula (I)

A-P(=O)(OX)—H    (I)

wherein

A is an ethyl, n-propyl, i-propyl, n-butyl, i-butyl, n-pentyl, i-pentyl, n-hexyl, i-hexyl, 2-phenylethyl, 1-phenylethyl, 3-phenylpropyl, 2-phenylpropyl, 2-hydroxyethyl, 3-hydroxypropyl, 2-carboxyethyl, 3-carboxypropyl, 2-acetatoethyl, 3-acetatopropyl, 2-butyratoethyl, 3-butyratopropyl, 2-ethyloxyethyl, 3-ethyloxypropyl, 2-propyloxyethyl, 3-propyloxypropyl, 2-butyloxyethyl, 3-butyloxypropyl, 3-carboxypropyl, 2-aminoethyl, 3-aminopropyl group or a combination thereof, and X is H, $C_1$-$C_{18}$-alkyl, $C_6$-$C_{18}$-aryl, $C_6$-$C_{18}$-arylalkyl, $C_6$-$C_{18}$-alkylaryl, $C_2$-$C_{18}$-alkylene, Mg, Ca, Al, Sb, Sn, Ge, Ti, Fe, Zr, Zn, Ce, Bi, Sr, Mn, Cu, Ni, Li, Na, K, H a protonated nitrogen base or a combination thereof, wherein the $C_1$-$C_{18}$-alkyl, $C_6$-$C_{18}$-aryl, $C_6$-$C_{18}$-arylalkyl, $C_6$-$C_{18}$-alkylaryl or $C_2$-$C_{18}$-alkylene is optionally substituted, and b) a diester-forming olefin of formula (II)

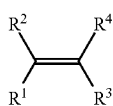

(II)

wherein $R^2$ $R^4$ are the same or different and are $CO_2H$, $CO_2R^5$, $R^6$-$CO_2H$ or $R^6$-$CO_2R^5$ and $R^1$, $R^3$ are the same or different and are H or $R^5$; or $R^1$, $R^4$ are the same or different and are $CO_2H$, $CO_2R^5$, $R^6$-$CO_2H$ or $R^6$-$CO_2R^5$ and $R^2$, $R^3$ are the same or different and are H or $R^5$; or $R^2$, $R^4$ are the same or different and are —CO-O-CO-, —CO-S-CO-, —CO-$NR^1$-CO-, or —CO-$PR^1$-CO- and $R^1$, $R^3$ are the same or different and are H or $R^5$; or $R^1$, $R^2$ are the same or different and are $CO_2H$, CN, $CO_2R^5$, $R^6$-$CO_2H$ or $R^6$-$CO_2R^5$ and $R^3$, $R^4$ are the same or different and are H or $R^5$; or $R^1$ $R^2$ are the same or different and are -$CR_2^3$—CO-O-CO-, —$CR_2^3$—CO-$NR^1$-CO-, —$CR_2^3$-CO-O-CO-$CR_2^3$ or —$CR_2^3$-CO-$NR^1$-CO-$CR_2^3$ and $R^3$, $R^4$ are the same or different and are H or $R^5$; or $R^2$ and $R^4$ each represent —CO-$CR^5$=$CR^5$-CO- and $R^1$, $R^3$ are the same or different and are H are R5;

$R^5$ is $C_1$-$C_{18}$-alkyl, $C_6$-$C_{18}$-aryl, $C_6$-$C_{18}$-arylalkyl or $C_6$-$C_{18}$-alkylaryl;

$R^6$ is $C_2$-$C_{18}$-alkylene, $C_6$-$C_{18}$-arylene, $C_6$-$C_{18}$-alkarylene, $C_6$-$C_{18}$-aralkylene or a combination thereof, wherein the composition is in the form of a flame retardant, a flame retardant for clearcoats or intumescent coatings, a flame retardants for wood or other cellulose-containing products, a reactive flame retardant for polymers, a nonreactive flame retardant for polymers, a flame-retardant polymeric molding composition, a flame-retardant polymeric molding, or a flame-retardant finishing of polyester or cellulose straight fabrics or blend fabrics by impregnation.

22. A flame-retardant thermoplastic or thermoset polymeric molding composition comprising 0.5% to 45% by weight of an adduct formed from a) an alkylphosphonous acid derivative of formula (I)

A-P(=O)(OX)—H    (I)

wherein

A is an optionally substituted $C_2$-$C_{18}$-alkyl, $C_2$-$C_{18}$-alkylene, $C_6$-$C_{18}$-arylalkyl, $C_6$-$C_{18}$-arylalkyl or a combination thereof, and X is H, $C_1$-$C_{18}$-alkyl, $C_6$-$C_{18}$aryl, $C_6$-$C_{18}$-arylalkyl, $C_6$-$C_{18}$-alkylaryl, $C_2$-$C_{18}$-alkylene, Mg, Ca, Al, Sb, Sn, Ge, Ti, Fe, Zr, Zn, Ce, Bi, Sr, Mn, Cu, Ni, Li, Na, K, H a protonated nitrogen base or a combination thereof, wherein the $C_1$-$C_{18}$-alkyl, $C_6$-$C_{18}$-aryl, $C_6$-$C_{18}$-arylalkyl, $C_6$-$C_{18}$-alkylaryl or $C_2$-$C_{18}$-alkylene is optionally substituted, and b) a diester-forming olefin of formula (II)

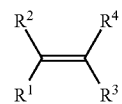

(II)

wherein $R^2$, $R^4$ are the same or different and are $CO_2H$, $CO_{2 R}^5$, $R^6$-$CO_2H$ or $R^6$-$CO_2R^5$ and $R^1$, $R^3$ are the same or different and are H or $R^5$; or $R^1$, $R^4$ are the same or different and are $CO_2H$, $CO_2R^5$, $R^6$-$CO_2H$ or $R^6$-$CO_2R^5$ and $R^2$, $R^3$ are the same or different and are H or $R^5$; or $R^2$, $R^4$ are the same or different and are —CO-O-CO-, —CO-S-CO-, —CO-$NR^1$-CO-, or —CO-$PR^1$-CO- and $R^1$, $R^3$ are the same or different and are H or $R^5$; or $R^1$, $R^2$ are the same or different and are $CO_2H$, CN, $CO_2R^5$, $R^6$-$CO_2H$ or $R^6$-$CO_2R^5$ and $R^3$, $R^4$ are the same or different and are H or $R^5$; or $R^1$, $R^2$ are the same or different and are —$CR_2^3$-CO-O-CO-, —$CR_2^3$-CO-$NR^1$-CO-, —$CR_2^3$-CO-O-CO-$CR_2^3$ or —$CR_2^3$-CO-$NR^1$-CO-$CR_2^3$ and $R^3$, $R^4$ are the same or different and are H or $R^5$; or $R^2$ and $R^4$ each represent —CO-$CR^5$=$CR^5$-CO- and $R^1$, $R^3$ are the same or different and are H are $R^5$;

$R^5$ is $C_1$-$C_{18}$-alkyl, $C_6$-$C_{18}$-aryl, $C_6$-$C_{18}$-arylalkyl or $C_6$-$C_{18}$-alkylaryl;

$R^6$ is $C_2$-$C_{18}$alkylene, $C_6$-$C_{18}$-arylene, $C_6$-$C_{18}$-alkarylene, $C_6$-$C_{18}$-aralkylene or a combination thereof, 0.5% to 99% by weight of a thermoplastic polymer thermoset polymer or mixtures thereof, 0% to 55% by weight of an additive and 0% to 55% by weight of a filler or reinforcing material, wherein the sum total of the components is 100% by weight.

23. A flame-retardant thermoplastic or thermoset polymeric molding, film, thread or fiber comprising 0.5% to 45% by weight of an adduct formed from
a) an alkylphosphonous acid derivative of formula (I)

$$A\text{-}P(=O)(OX)\text{—}H \quad \text{(I)}$$

wherein
A is an optionally substituted $C_2$-$C_{18}$-alkyl, $C_2$-$C_{18}$alkylene, $C_6$-$C_{18}$-arylalkvl, $C_6$-$C_{18}$-arylalkyl or a combination thereof, and
X is H, $C_1$-$C_{18}$-alkyl, $C_6$-$C_{18}$-aryl, $C_6$-$C_{18}$-alkylaryl, $C_2$-$C_{18}$-alkylene, Mg, Ca, Al, Sb, Sn, Ge, Ti, Fe, Zr, Zn, Ce, Bi, Sr, Mn, Cu, Ni, Li, Na, K, H a protonated nitrogen base or a combination thereof, wherein the $C_1$-$C_{18}$-alkyl, $C_6$-$C_{18}$-aryl, $C_6$-$C_{18}$-arylalkyl, $C_6$-$C_{18}$-alkylaryl or $C_2$-$C_{18}$-alkylene is optionally substituted, and
b) a diester-forming olefin of formula (II)

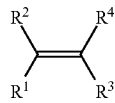
(II)

wherein $R^2$, $R^4$ are the same or different and are CO2H, $CO_2R^5$, $R^6$-$CO_2H$ or $R^6$-$CO_2R^5$ and $R^1$, $R^3$ are the same or different and are H or $R^5$; or
$R^1$, $R^4$ are the same or different and are $CO_2H$, $CO_2R^5$, $R^6$-$CO_2H$ or $R^6$-$CO_2R^5$ and
$R^2$, $R^3$ are the same or different and are H or $R^5$; or
$R^2$, $R^4$ are the same or different and are —CP-O-CO-, —CO-S-CO-, —CO-$NR^1$-CO-, or —CO-$PR^1$-CO- and $R^1$, $R^3$ are the same or different and are H or $R^5$; or
$R^1$, $R^2$ are the same or different and are $CO_2H$, CN, $CO_2R^5$, $R^6$-$CO_2H$ or $R^6$-$CO_2R^5$ and
$R^3$, $R^4$ are the same or different and are H or $R^5$; or
$R^1$, $R^2$ are the same or different and are —$CR_2^3$-CO-O-CO-, —$CR_2^3$-CO-$NR^1$-CO-, —$CR_2^3$-CO-O-CO-$CR_2^3$ or —$CR_2^3$-CO-$NR^1$-CO-$CR_2^3$ and $R^3$, $R^4$ are the same or different and are H or $R^5$; or
$R^2$ and $R^4$ each represent —CO-$CR^5$=$CR^5$-CO- and $R^1$, $R^3$ are the same or different and are H are $R^5$;
$R^5$ is $C_1$-$C_{18}$-alkyl, $C_6$-$C_{18}$-aryl, $C_6$-$C_{18}$-arylalkyl or $C_6$-$C_{18}$-alkylaryl; $R^6$ is $C_2$-$C_{18}$-alkylene, $C_6$-$C_{18}$-arylene, $C_6$-$C_{18}$-alkarylene, $C_6$-$C_{18}$-aralkylene or a combination thereof, 0.5% to 99% by weight of a thermoplastic polymer thermoset polymer or mixtures thereof, 0% to 55% by weight of an additive and 0% to 55% by weight of a filler or reinforcing material, wherein the sum total of the components is 100% by weight.

* * * * *